(12) United States Patent
Schmidt et al.

(10) Patent No.: US 6,413,936 B1
(45) Date of Patent: *Jul. 2, 2002

(54) GLYCOMIMETICS AS SELECTIN ANTAGONISTS AND PHARMACEUTICALS HAVING ANTIINFLAMMATORY ACTIVITY

(75) Inventors: Wolfgang Schmidt, Frankfurt; Ulrich Sprengard, Gustavsburg; Gerhard Kretzschmar, Eschborn; Robert Klein, Frankfurt; Horst Kunz, Mainz, all of (DE)

(73) Assignee: Glycorex AB, Lund (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/739,855

(22) Filed: Oct. 30, 1996

(30) Foreign Application Priority Data

Oct. 30, 1995 (DE) ......................................... 195 40 388

(51) Int. Cl.$^7$ ................................................ A61K 31/70
(52) U.S. Cl. ................................. 514/23; 514/8; 514/9; 536/1.11; 549/200; 549/356; 562/459; 585/275
(58) Field of Search ................... 514/8, 9, 23; 549/200, 549/356; 585/275; 562/459; 536/1.11

(56) References Cited

U.S. PATENT DOCUMENTS 5,604,207 A * 2/1997 DeFrees et al. ................ 514/25

FOREIGN PATENT DOCUMENTS

| WO | 94/24145 | 10/1994 |
| WO | 94/26700 | 11/1994 |
| WO | 95/04526 | 2/1995 |
| WO | 95/04751 | 2/1995 |
| WO | 95/10296 | 4/1995 |
| WO | 96/05209 | 2/1996 |

OTHER PUBLICATIONS

Noritsina, M.V.; Klochkova, I.N.; Bykovskaya, T. Khim. Geterosikl. Soedin. 1976, 2, 186–90. English language abstract CAPLUS Document No. 84:179955.*
Thewalt, K.; Rudolph, W. Fette, Seifen, Anstrichmittel 1963, 65, 601–3.*
Cologne, J; Jeltsch, P. Bull. Soc. Chim. France 1963, 6, 1288–92.*
Til, Z.V.; Markushina, I.; Sapunar, K; Ponomarev, A.A. Zhur. Obschchei Khim. 1957, 27(1), 110–17, In English translation.*
Wild et al. (1986) Liebigs Ann. Chem. 9: 1548–1567.
M. N. Blaude et al., "Interaction Between Aflatoxin B$_1$ and Oxytetracycline in Isolated Rat Hepatocytes", Cell Biology and Toxicology, vol. 6, No. 4, (1990).*

G. Walz et al., "Recognition by ELAM–1 of the Sialyl–Le$^x$ Determinant on Myeloid and Tumor Cells" Science, vol. 250, (Nov. 1990).*
H. C. Kolb et al., "Toward an Understanding of the High Enantioselectivity in the Osmium–Catalyzed Asymmetric Dihydroxylation (AD). 1.Kinetics", J. Am. Chem. Soc., vol. 116, (1994).*
W. Zhang et al., "Enantioselective Epoxidation of Unfunctionalized Olefins Catalyzed by (Salen) Manganese Complexes", J. Am. Chem. Soc., vol. 112, (1990), pp. 2801–2803.*
R. C. Larock et al., "Regioselective, Palladium–Catalyzed Hetero– and Carboannulation of 1,2–Dienes Using Functionally Subustituted Aryl Halides", J. Org. Chem., vol. 56, (1991).*
M. Yoshida et al., "Synthesis of Chemically Modified Sialic Acid–containing Sialyl–Le$^x$ Ganglioside Analogues Recognized by the Selectin Family", Glycoconjugate Journal, vol. 10, p. 3–15, (1993).*
B. K. Brandley et al., "Structure–Function Studies on Selectin Carbohydrate Ligands. Modificatins to Fucose, Sialic Acid and Sulphate as a Sialic Acid Replacement", Mycobiology, vol. 3, No. 6, (1993), pp. 633–639.*
M. D. Menger et al., "Scope and Perspectives of Intravital Microscopy–Bridge Over from in vitro to in vivo", Immunology Today, vol. 14, No. 11, (1993).*
J. H. Musser et al., "Structure–Activity Studies Based on the Sialyl Lewis X Epitope", Trends in Receptor Research, (1993).
J. M. Harlan, "Leukocyte–Endothelial Interactions", The Journal of the American Society of Hematology, vol. 65, No. 3, (Mar., 1985), pp. 513–525.
D. E. Levy et al., "Synthesis of Novel Fused Ring C–Glycosides", Tetrahedron: Asymmetry, vol. 5, No. 11, p. 2265–2268, (1994).
N. M. Allanson et al., "The Synthesis of Novel Mimics of the Sialyl Lewis X Determinant", Tetrahedron: Asymmetry, vol. 5, No. 11, p. 2061–2076, (1994).
J. Bajorath et al., "CD62/P–Selectin Binding Sites for Myeloid Cells and Sulfatides Are Overlapping", Biochemistry, vol. 33, p. 1332, (1994).
K. L. Moore et al., "The P–Selectin Glycoprotein Ligand from Human Neutrophils Displays Sialylated, Fucosylated, O–Linked Poly–N–Acetyllactosamine", J. Bio. Chem., vol. 269, No. 37, p. 23318–23327, (Sep. 1994).
T. Uchiyama et al., "Design and Synthesis of Sialyl Lewis X Mimetics", J. Am. Chem. Soc., vol. 117, p. 5395–5396, (1995).
T. A. Springer, "Adhesion Receptors of the Immune System", Nature, vol. 346, p. 425–434, (Aug., 1990).

(List continued on next page.)

Primary Examiner—Kathleen K. Fonda
(74) Attorney, Agent, or Firm—Foley & Lardner

(57) ABSTRACT

The invention relates to novel mimetics of the tetrasaccharides sialyl-Lewis-X and sialyl-Lewis-A having an improved action as inhibitors of cell adhesion, to a process for the preparation of these compounds and to their use as pharmacological active compounds and diagnostic agents.

7 Claims, No Drawings

OTHER PUBLICATIONS

E. L. Berg et al., "L–Selectin–Mediated Lymphocyte Rolling on MAdCAM–1", Nature, vol. 366. (Dec. 1993).

S. Baumhueter et al., "Binding of L–Selectin to the Vascular Sialomucin CD34", Science, vol. 262, p. 436–438, (Oct. 1993).

M. S. Mulligan et al., Protective Effects of Oligosaccharides in P–Selectin–Dependent Lung–Injury, Nature, vol. 364, p. 149–151, (Jul. 1993).

K. Drew et al., "C–Glycoside Synthesis II: Herny Condensations of 4,6–O–Alkylidene Pyranoses with A 1,3–Proton Transfer Catalyst– A Route to Blocked Aminomethyl–C–Glycosides", Tetrahedron, vol. 47, No. 32, p. 6113–6126, (1991).

M. D. Lewis et al., "Highly Stereoselective Approaches to α– and β–C–Glycopyranosides", J. Am. Chem. Soc., vol. 104, p. 4976–4978, (1982).

R. M. Nelson et al., "Higher–Affinity Oligosaccharide Ligands for E–Selectin", The American Society for Clinical Investigation, vol. 91, p. 1157–1165, (Mar. 1993).

A. Atherton et al., "Quantitative Investigations of the Adhesiveness of Circulating Polymorphonuclear Leucocytes to Blood Vessel Walls", J. Physiol., vol. 222, p. 447–474, (1972).

S.J. Foster et al., "Production of TNFα by LPS–Stimulated Murine, Rat and Human Blood and its Pharmacological Modulation", Agents Action, vol. 38, p. C76–C78, (1993).

M. Buerke et al., "Sialyl Lewis– Containing Oligiosaccharide Attenuates Myocardial Reperfusion Injury in Cats", J. Clin. Invest., vol. 93, p. 1140–1148 (Mar. 1994).

D. Bruneel et al., "Chemical Modification of Pullulan: Chloroformate Activation", Polymer, vol. 34 No. 12, p. 2633–2637, (1993).

A. Aruffo et al., "CD62/P–Selectin Recognition of Myeloid and Tumor Cell Sulfatides", Cell, vol. 67, (Oct. 1991).

* cited by examiner

GLYCOMIMETICS AS SELECTIN ANTAGONISTS AND PHARMACEUTICALS HAVING ANTIINFLAMMATORY ACTIVITY

FIELD OF THE INVENTION

The invention relates to novel mimetics of the tetrasaccharides sialyl-Lewis-X (SLeX) and sialyl-Lewis-A (SLeA) with improved action as inhibitors of cell adhesion, to a process for the preparation of these compounds and to their use as pharmacological active compounds and diagnostic agents.

BACKGROUND OF THE INVENTION

The circulation of blood cells, for example leukocytes, neutrophils, granulocytes and monocytes, is, at the molecular level, a highly complex multistage process of which only individual steps are known (for a review see: Springer, Cell 76:301–314 (1994)). Recent research has shown that both localization of neutrophils and monocytes at foci of inflammation and lymphocyte recirculation, which is crucial in immune monitoring, respond to very similar molecular mechanisms. Thus, in acute and chronic inflammatory processes leukocytes adhere to endothelial cells and migrate to the focus of inflammation and into the secondary lymphatic organs. This process involves numerous specific signal molecules, for example interleukins, leukotrienes and tumor necrosis factor (TNF), G-protein coupled receptors and, in particular, tissue-specific cell adhesion molecules, which precisely control immune cell and endothelial cell recognition. The most important adhesion molecules involved in this process, designated below as receptors, include the selectins (E-, P- and L-selectins), integrins and the members of the immunoglobulin superfamily.

Adhesion of leukocytes to endothelial cells is mediated by selectin receptors in the initial phase of inflammatory processes, and is a natural and necessary immune response to various inflammatory stimuli and to vascular tissue damage. The course of a variety of acute and chronic disorders, such as rheumatism, reperfusion injuries such as myocardial ischemia/infarct (MI), acute pneumonia following surgery, traumatic shock and stroke, psoriasis, dermatitis, ARDS (adult respiratory distress syndrome) and restenosis following surgical intervention (for example angioplasty and by-pass operations) is, however, adversely affected by excessive leukocyte adhesion and infiltration into affected tissue. Controlling this adhesion process at a very early stage of inflammation is, therefore, a highly attractive and generally applicable concept for the pharmacological control of inflammatory disorders.

The tetrasaccharides sialyl-Lewis-X (SLeX) and sialyl-Lewis-A (SLeA), which occur as substructures of glycosphingolipids and glycoproteins on cell membranes, can function as ligands for all three selectin receptors. A series of glycoproteins, mucins and glycolipids are known to be suitable endogenous ligands for the selecting. These include: Mucosal Vascular Addressin MadCAM-1 (Berg et al., Nature 366:695 (1993)) and Sialomucin CD34 (Baumhuter et al., Science 262:436 (1993)) for L-selectin: O-linked polylactosamine-sialomucin PSGL-1 on human neutrophils for P-selectin (Moore et al., J.Biol.Chem. 269:23318 (1994); and N-linked sialoglycoproteins of the ESL-1 type for E-selectin (Vestweber et al., Cell Biol. 121:449 (1993)).

The specificity of these and other potential ligands for selectins in vivo has not yet been elucidated. The tetrasaccharides SLeX and SLeA represent only a substructure of the substantially more complex structures of endogenous selectin ligands and, because of their similar affinity for selecting, cannot alone account for receptor binding specificity. Due to the structural complexity of SLeX and SLeA, the use of simpler, structurally modified mimetics as antagonists for modulating or suppressing excessive leukocyte adhesion is a promising therapeutic starting point for a strategy for alleviating or healing the above-mentioned disorders mentioned.

SLeX has already been used successfully in animal experiments to protect against P-selectin-dependent lung damage (Mulligan et al., Nature 364:149 (1993)) and against myocardial reperfusion injuries (Buerke et al., J.Clin.Invest. 93:1140 (1994)). In initial clinical trials against acute pneumonia, the compound was employed in a dose of 1–2 grams per day per patient (report by Cytel Corp./La Jolla (Calif.) at the 2nd Glycotechnology Meeting/CHI in La Jolla/USA on May 16–18, 1994).

Some publications and patent applications have also reported efforts to obtain more potent antagonists by structural variation of the ligand. The aim of such work is to provide more effective antagonists that potentially would also be suitable for use in vivo at a relatively low dose. Variation of the fucose and neuraminic acid units regarded as crucial for the structure-activity relationship (Brandley et al., Glycobiology 3:633 (1993); Yoshida et al., Glycoconjugate J. 10:3 (1993)), did not, however, afford significantly improved inhibition. Only when the glucosamine unit was varied (replacement of GlcNAc by glucose and azido groups and amino groups in position 2 of GlcNAc) was significantly increased affinity for the E-selectin receptor achieved. By contrast, improved binding of the P-selectin receptor was not achieved.

In general, all previous successes have been limited to improving the binding affinity of SLeX and SLeA derivatives for the E-selectin receptor, since at inhibitor concentrations of about 1 mM only weak inhibitory effects with the P-selectin receptor have been found (Nelson et al., J.Clin.Invest. 91:1157 (1993)). The binding affinities of modified SLeX/A structures for selecting has been reviewed. See Pharmacochem. Libr. 20 (1993))(Trends in Drug Research), pp. 33–40.

In addition to their low affinity for selectin binding, these compounds all contain at least one unstable glycosidic linkage, which severely restricts their oral availability as active compounds. This instability also greatly limits the synthesis of various derivatives, since the hydrolytic lability of the glycosidic linkage limits the available reaction conditions. A number of strategies for synthesizing mimetics have been developed to obtain an increase in hydrolytic stability.

For example, stability has been increased by attaching the side chain via a C—C bond to the C-4 carbon of fucose (Floyd et al., Tetrahedron Asymmetry 5:2061 (1994).

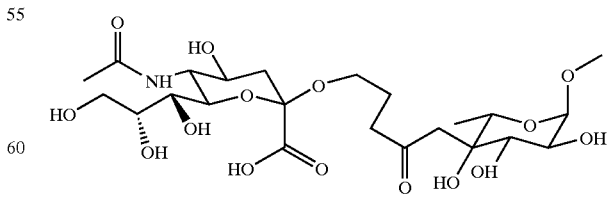

In this case, however, the linkage to C-4 of fucose caused the orientation of the side chain to differ from that of the natural ligand, and only low affinity for selectin binding was observed.

Use of carbocyclic carbohydrate analogs where the side chain linkage is through a C—C bond to C-1 would give a conformation similar to that of the natural ligand that also would be stable against degradation. Several carbocyclic carbohydrate analogs of monosaccharide units have been prepared. Thus, for example, activated monosaccharides have been reacted with nitromethane (Gross, *Tetrahedron* 47:6113 (1991)), allylsilane (Kishi et al., *J. Am. Chem. Soc.* 104:4976–4978 (1982)), and olefins (Levy et al., *Tetrahedron Asymmetry* 5:2265–2268 (1994)). The functionality introduced into these monosaccharides makes them suitable as a unit for further coupling operations.

Use of a carbocyclic analog as a building block for selectin antagonists has been shown to lead to a mimetic with affinity for selectins. It was possible at the same time, by reacting a fucose unit with allylsilane, to synthesize a specific C-glycosidic unit (1) with an α-orientation at the side chain (WO 95/04751). Selectivities in the allylation are high, with α/β=14/1, but scale-up of the reaction is difficult due to the conditions employed, particularly the need to use 10 equivalents of volatile and highly corrosive trimethylsilyl triflate. Similarly, chromatographic purification of the product is required, although it is not possible to separate the α/β mixture.

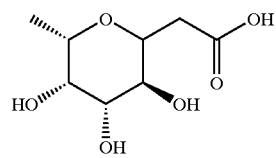

1

The terminal acid function of the side chain can be used to synthesize glycopeptide analogs, for example (2). These analogs have $IC_{50}$ values of about 1 mM, but are unstable to proteolytic degradation. Consequently, despite stabilization of the sugar unit by the C-glycoside, the oral availability of these compounds continues to be severely restricted. A further disadvantage is the presence of the unwanted β compound, which cannot be separated. These β derivatives show no activity, due to the side chain having the wrong orientation, as demonstrated by corresponding model calculations.

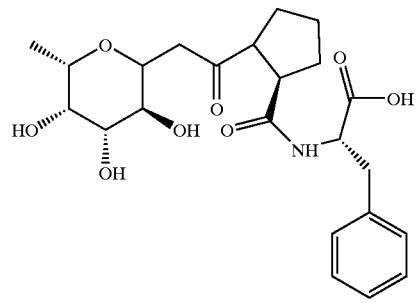

2

The C-glycosidic unit (1) has also been used in an analogous manner, for synthesizing various other mimetics intended to imitate the active conformation of SLeX. The compounds tested, for example (3), however, exhibited $IC_{50}$ values of 10–20 mM, higher by a factor of 10–20 than that of the natural ligand SLeX (Wong, et al., *J. Am. Chem. Soc.* 117:5395(1995)).

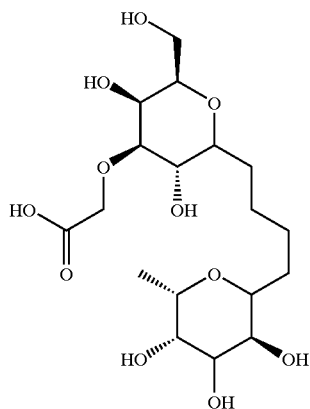

3

Use of a substituted allylsilane allowed preparation of a C-glycoside.

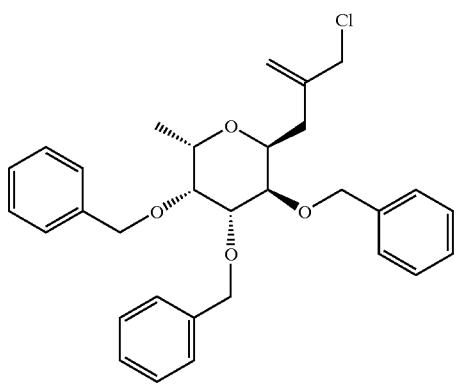

4

By linking to triterpenoid acid derivatives (Betulinic Acid: WO 95/04526; Glycyrrhetinic Acid: WO 94/24145), mimetics such as (4a) were prepared. These were intended to have a multi-medicament capacity and were tested in a variety of test systems (inhibition of 5-lipoxygenase, antimetastatic action, P-selectin inhibition). In this case an $IC_{50}$ of 0.75 mM for binding to P-selectin was obtained. It should be noted, however, that the triterpenoid acid alone displayed an $IC_{50}$ of 0.125 mM.

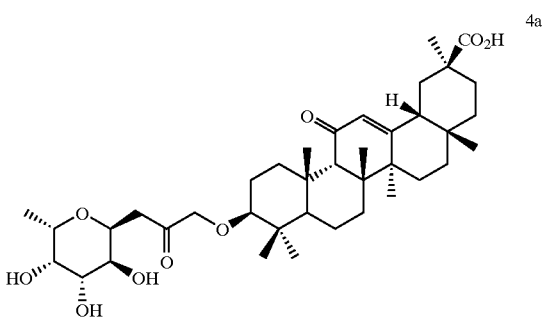

4a

Preparation of the C-glycoside unit (4) likewise required a complex chromatographic purification, where the β derivative was separated only with difficulty. Additionally, stability of the C-glycoside was limited due to the reactive allylic chloride group.

In addition to the preparative problems described above (such as complex chromatographic purification, multiple synthetic steps due to protective-group strategy, α/β mixtures) the aforementioned C-glycoside mimetics displayed a selectin binding affinity too low for effective inhibition of adhesion processes. In addition to stability problems with a fucose mimetic, the low affinity of the aforementioned derivatives is also due to the need for correct orientation and fixed conformation of side chains that is important for selectin binding, which the derivatives apparently do not satisfy.

According to L. A. Lasky, negatively charged sialic acid (or a negatively charged sulfonic acid group) is an absolute requirement for binding to selectins. Studies to determine potential binding sites have already been carried out using the recently elucidated crystal structure of E-selectin. Possible binding sites for the sialic acid function have been proposed, including the two lysines K111 and K113 (Bajorath et al., *Biochemistry* 33:1332 (1994)) and Arg 97, Lys 111 and Lys 113 (*Structural Biology* 1:140 (1994)).

It is apparent, therefore, that readily prepared, stable, low molecular weight mimetics of sialyl-Lewis-X and sialyl-Lewis-A structures possessing significantly enhanced affinity for selectins are greatly to be desired. It is also greatly desirable that these mimetics possess a structure that makes them suitable for oral administration.

SUMMARY OF THE INVENTION

It is therefore an object of the present invention to provide stable, low molecular mass mimetics of sialyl-Lewis-X and sialyl-Lewis-A structures, respectively, whose constitution and configuration possess a significantly enhanced affinity for selecting, which are easier to obtain by synthesis than oligosaccharides and whose structure makes them suitable as pharmaceuticals with potential for oral availability.

These and other objects of the invention are achieved by providing a compound of the formula I

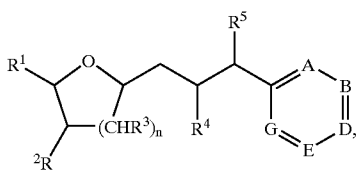

in which n is 1 or 2; $R^1$ is —H, —CH$_2$OH or —CH$_3$; $R^2$ and $R^3$ independently of one another are —H or —OH; $R^4$ and $R^5$ independently of one another are —H, —OH—, -alkyl, —O-alkyl, —S-alkyl, —NH$_2$, —NH-alkyl, —N(alkyl)$_2$, —NH-aryl, —N(aryl)$_2$, —OSO$_3$H, —(CH$_2$)$_r$—COOH, —(CH$_2$)$_r$—COO-alkyl, —(CH$_2$)$_r$CH(COO-alkyl)$_2$, —(CH$_2$)$_r$CH(COOH)$_2$, —(CH$_2$)$_{r-NH2}$, where r is an integer from zero to ten, or $R^4$ and $R^5$ together form a double bond or an epoxide ring; A, B, D, E and G independently are $CR^6$, $CR^7$, $CR^8$, $CR^9$, $CR^{10}$ or nitrogen, provided that only one of the variables A, B, D, E and G may be nitrogen; $R^6$, $R^7$, $R^8$, $R^9$ and $R^{10}$ independently of one another are —H, -alkyl, —OH, —O-alkyl, —NH$_2$, —NH-alkyl, —N(alkyl)$_2$, —NH-aryl, —N(aryl)$_2$, —F, —Cl, —Br, —I, —COO-alkyl, —CO—NH$_2$, —COOH, —OSO$_3$H, 4-hydroxypiperidin-4-yl, —(CH$_2$)$_m$—COOH, —(CH$_2$)$_m$COO-alkyl, —(CH$_2$)$_m$—CH(COO-alkyl)$_2$, —(CH)$_m$—CH(COOH)$_2$, where m is an integer from zero to ten, —(CH$_2$)$_p$—NH$_2$, where p is an integer from one to ten, a group of the formula II, III, IV, V, VI, or VII,

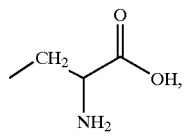

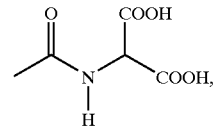

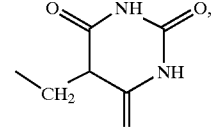

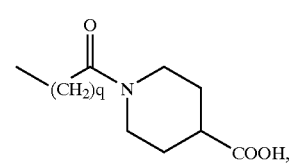

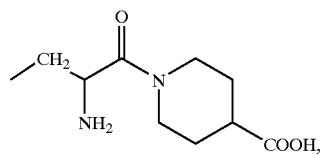

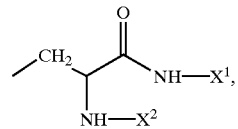

where $X^1$ and $X^2$ independently are H or an oligopeptide, or two of $R^6$, $R^7$, $R^8$, $R^9$ or $R^{10}$, provided that they are adjacent, together form a carboxymethyl-substituted imidazole ring or a crown ether ring.

In accordance with one aspect of the invention, $R^1$, $R^2$, and $R^3$ have the same absolute configuration as in L-fucose, D-mannose, or D-ribose. In a preferred embodiment $R^4$ and $R^5$ are both H, or $R^4$ and $R^5$ together from a double bond. In another preferred embodiment, one of the variables A, B, G, E or D is selected from the group consisting of C—COOH, C—CH$_2$—COOH, C—CH(COOH)$_2$, and NH$_2$, and all of the other of these variables are C—H. In yet another preferred embodiment, the variables A, D and G are C—H, the variable B is nitrogen and the variable E is C—CH$_2$—COOH. In still another preferred embodiment, A,B, G and E are C—H and D is $CR^8$.

In accordance with another aspect of the invention, there is provided compounds where $R^8$ is selected from the group consisting of II, III, IV, V, VI, and VII. In a preferred embodiment, $R^8$ is VII, and $X^1$ and $X^2$ independently of one another are H or an oligopeptide. In other preferred embodiments, $R^8$ is II or IV. In another preferred embodiment, the oligopeptide comprises L-amino acids, and preferably comprises the sequence arg-gly-asp-ser.

In accordance with yet another aspect of the invention, there are provided compounds where one of the variables A,B, G, E and D is $CR^9$ and all of the other of these variables are C—H. In a preferred embodiment, $R^9$ is a 4-hydroxypiperidin-4-yl group.

In accordance with still another aspect of the invention there are provided compounds where E and G together form a substituted imidazole ring and A, B and D are C—H.

In accordance with a still further aspect of the invention there are provided compounds where A and B are C—H, G and E are C—OH and D is C—COOH.

In accordance with another aspect of the invention there is provided a method for preparing a compound of the type described above, comprising reacting a compound of the formula VIII,

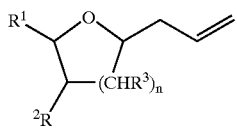

VIII where $R^1$, $R^2$ and $R^3$ are present in protected or unprotected form, with a compound of the formula IX,

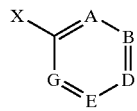

IX where X is halogen, and G and E are linked by a single or a double bond, in the presence of a transition metal catalyst. In one preferred embodiment, $R^1$, $R^2$ and $R^3$ are unprotected. In another preferred embodiment, the transition metal catalyst is a palladium catalyst.

In accordance with yet another aspect of the invention there is provided a pharmaceutical composition comprising a compound as set forth above, together with a pharmaceutically acceptable excipient.

In accordance with still aspect of the invention there is provided a method of treating a disease associated with excessive selectin-mediated cell adhesion, comprising administering a pharmaceutical composition as set forth above to a patient suffering from said disease.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF PREFERRED EMBODIMENTS

The present invention provides novel glycomimetics that bind to both E- and P-selectin, and that possess antiinflammatory activity. These glycomimetics have structures that are variants of the natural ligands sialyl Lewis X and sialyl Lewis A, but have enhanced stability against degradation in vitro and in vivo. Moreover, the glycomimetics are readily prepared in quantity by organic synthesis methods well known in the art. The invention also includes pharmaceutical compositions comprising an effective amount of at least one of the glycomimetics of the invention in combination with a pharmaceutically acceptable sterile vehicle, as described, for example, in Remingtons' Pharmaceutical Sciences; Drug Receptors and Receptor Theory, 18th ed., Mack Publishing Co., Easton, Pa. (1990). Compounds according to the present invention, and their physiologically tolerated salts, are suitable for use as medicaments in mammals, especially humans.

The glycomimetics of the present invention may generally be represented by the formula I

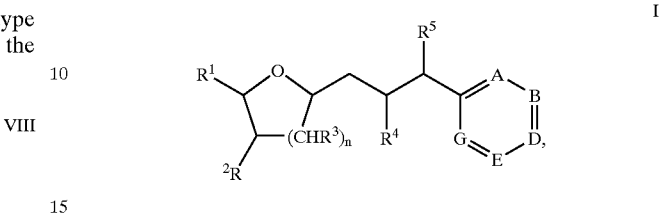

I

In this formula, $R^1$ is —H, —CH$_2$OH or —CH$_3$, $R^2$ and $R^3$ independently of one another are —H or —OH, and n is 1 or 2. $R^4$ and $R^5$ independently of one another are —H, —OH-, -alkyl, —O-alkyl, —S-alkyl, —NH$_2$, —NH-alkyl, —N(alkyl)$_{21}$, —NH-aryl, —N(aryl)$_2$, —OSO$_3$H, —(CH$_2$)$_r$—COOH, —(CH$_2$)$_r$—COO-alkyl, —(CH$_2$)$_r$CH(COO-alkyl)$_2$, —(CH$_2$)$_r$CH(COOH)$_2$,—or (CH$_2$)$_{r-NH2}$. r is an integer from zero to ten. $R^4$ and $R^5$ may also together form a double bond or an epoxide ring.

A, B, D, E and G are CR$^6$, CR$^7$, CR$^8$, CR$^9$, CR$^{10}$ or nitrogen, provided that in each case only one of the variables A, B, D, E and G is nitrogen. $R^6$, $R^7$, $R^8$, $R^9$ and $R^{10}$ independently of one another are —H, -alkyl, —OH, —O-alkyl, —NH$_2$, —NH-alkyl, —N(alkyl)$_2$, —NH-aryl, —N(aryl)$_2$, —F, —Cl, —Br, —I, —COO-alkyl, —CO—NH$_2$, —COOH, —OSO$_3$H, 4-hydroxypiperidin-4-yl, —(CH$_2$)$_m$—COOH, —(CH$_2$)$_m$COO-alkyl, —(CH$_2$)$_m$—CH(COO-alkyl)$_2$, —(CH$_2$)$_m$— or CH(COOH)$_2$, where m is an integer from zero to ten. $R^6$, $R^7$, $R^8$, $R^9$ and $R^{10}$ also can be —(CH$_2$)$_p$—NH$_2$, where p is an integer from one to ten. Alternatively, $R^6$, $R^7$, $R^8$, $R^9$ and $R^{10}$ independently of one another can be selected from the group consisting of moieties having the structures II, III, IV, V, VI, or VII. In formula V, q is an integer from one to ten. In formula VII, $X^1$ and $X^2$ independently of one another are H or an oligopeptide. Alternatively, $X^1$ and $X^2$ independently are two of the variables $R^6$, $R^7$, $R^8$, $R^9$ and $R^{10}$, that, provided they are adjacent, together form a carboxymethyl-substituted imidazole ring or a crown ether ring, with the other variables being as defined above.

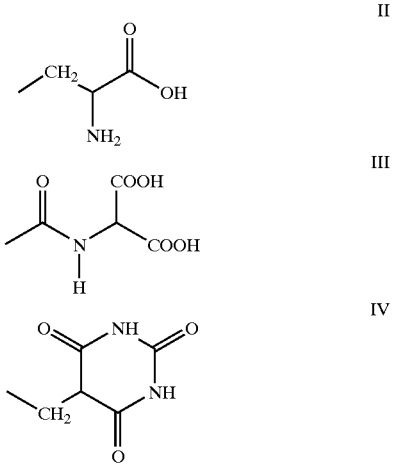

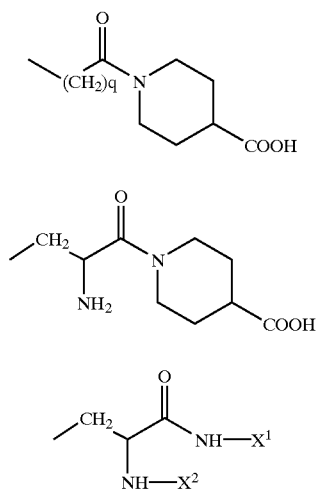

In a preferred embodiment of the invention, in a compound of the formula I, one of the variables A, B, G, E and D is C—COOH and the other variables are C—H. Examples of such embodiments are compounds having the formulae 16, 21, 22a, 23, or 29

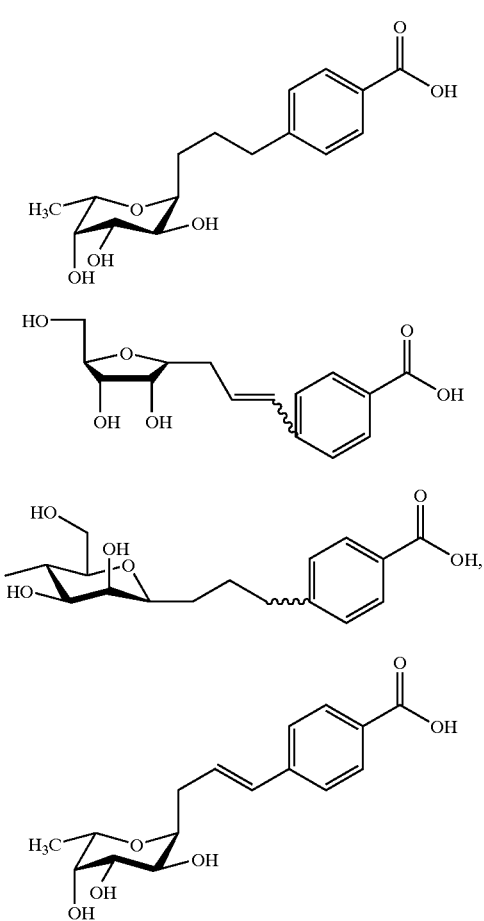

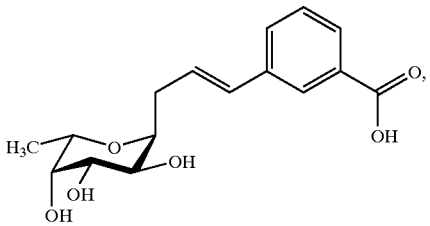

In another preferred embodiment one of the variables A, B, G, E and D is C—CH$_2$—COOH and the other variables are C—H. Examples of these embodiments are compounds 28 and 28a:

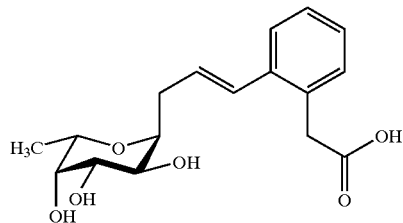

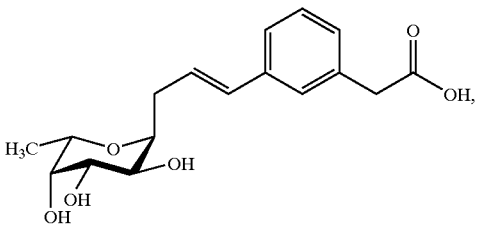

In another preferred embodiment, one of the variables A, B, G, E and D is C—CH—(COOH)$_2$ and the other variables are C—H. An example of such an embodiment is compound 24:

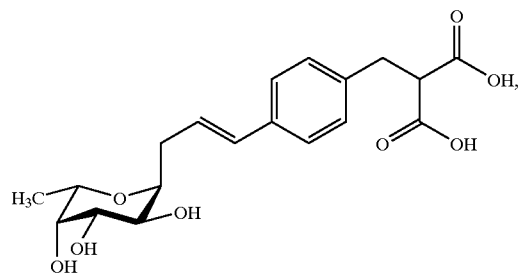

In yet another preferred embodiment, one of the variables A, B, G, E and D is C—NH$_2$ and the other variables are C—H. Examples of these embodiments are compounds 27 and 30:

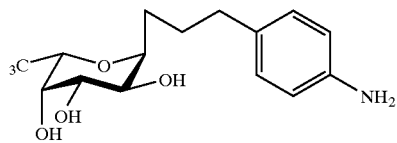
27

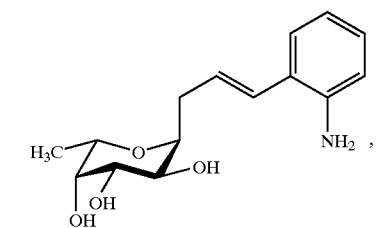
30

In still another preferred embodiment, the variables A, D and G are C—H, B is nitrogen and E is C—CH$_2$—COOH, for example, compound 26:

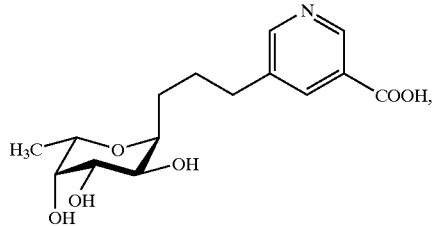
26

Alternatively, A, B, G and E are C—H and D is CR$^8$. R$^8$ is preferably a moiety having the formula II

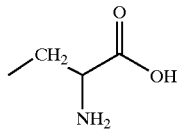
II

An example of such an embodiment is compound 20:

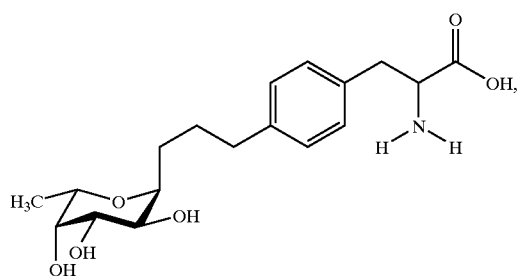
20

Alternatively, R$^8$ is a group having the formula III

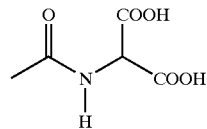
III

An example of such an embodiment is compound 18:

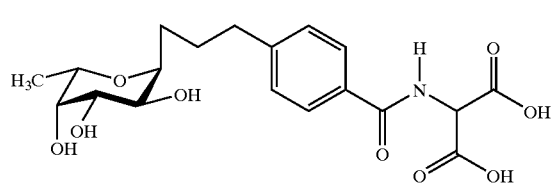
18

In another alternative, R$^8$ is a moiety having the formula IV

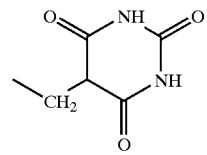
IV

An example of such an embodiment is compound 25:

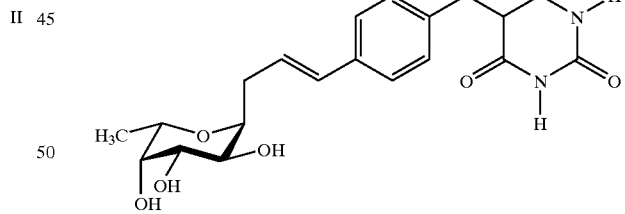
25

In still another alternative, R$^8$ is a moiety having the formula V, where q is an integer from one to ten,

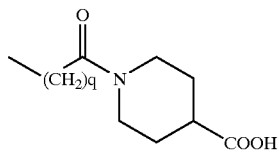
V

An example of such an embodiment is compound 34:
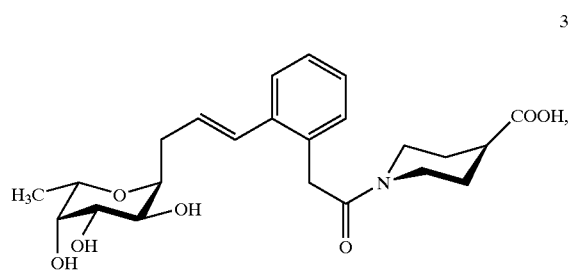
In another alternative, $R^8$ is a group of the formula VI:
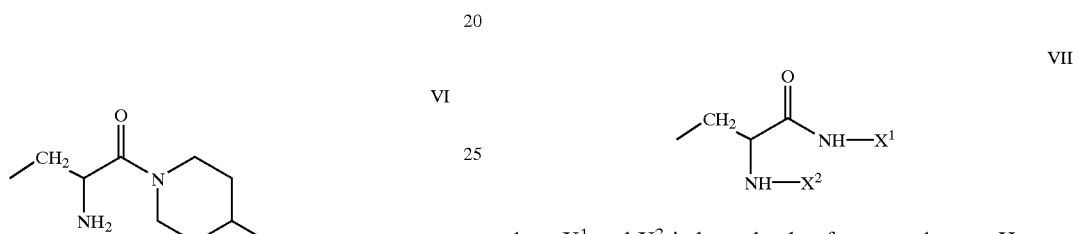
An example of such an embodiment is compound 33:
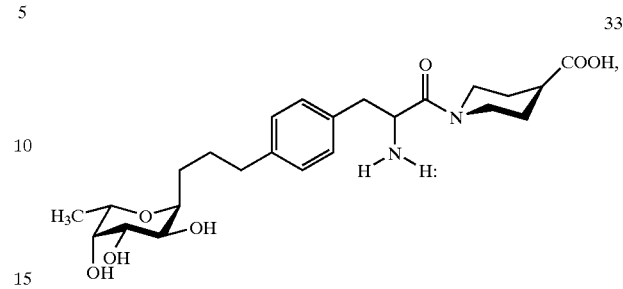
$R^8$ may also be a group having the formula VII
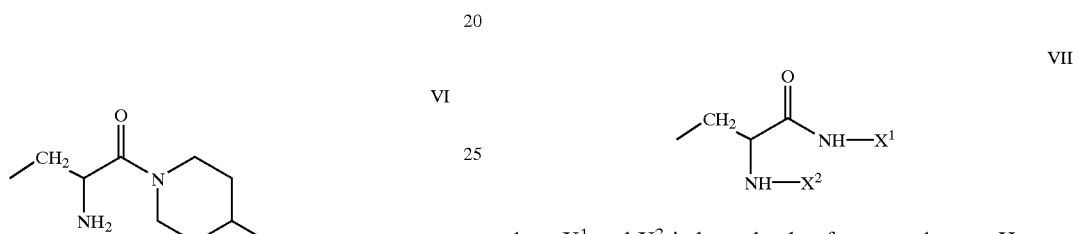
where $X^1$ and $X^2$ independently of one another are H or an oligopeptide. An example of such an embodiment is compound 36:
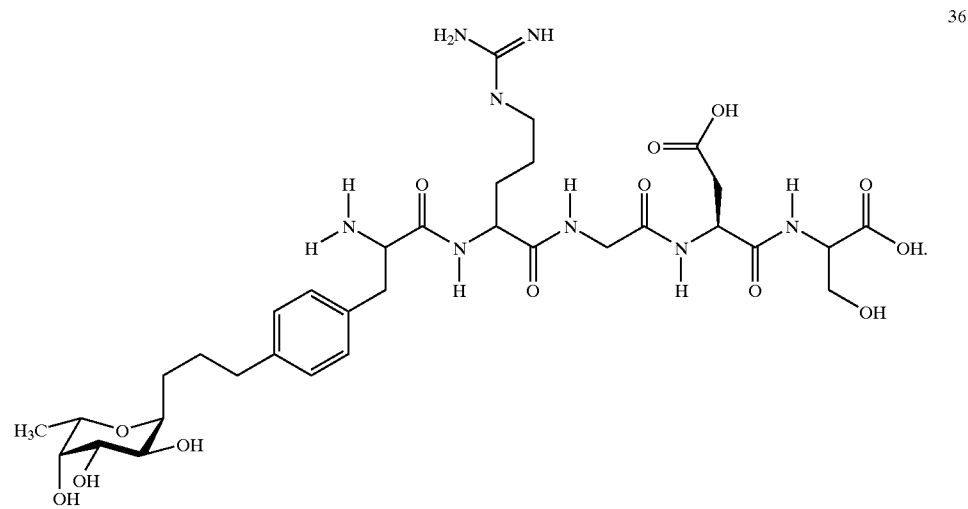

In other preferred embodiments, one of the variables A, B, G, E and D is $CR^9$ and the other variables are C—H. Preferably, $R^9$ is a 4-hydroxypiperidin-4-yl group, for example compound 32:

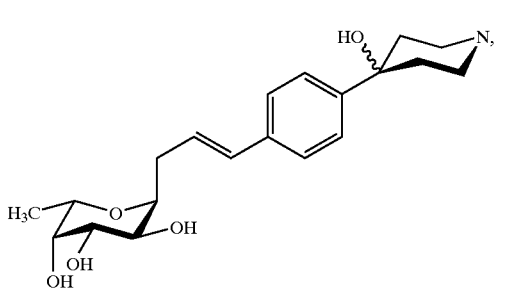

Alternatively, E and G together form a substituted imidazole ring and A, B and D are C—H, for example compound 31:

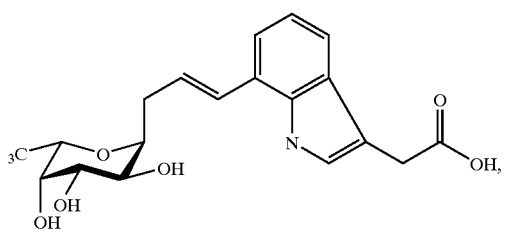

In yet another embodiment, A and B are C—H, G and E are C—OH and the D is C—COOH, for example compound 37:

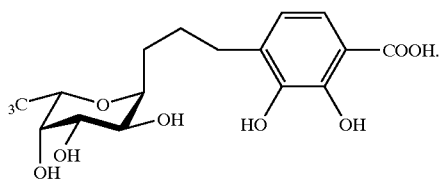

Glycomimetics according to the present invention may be prepared by reacting a compound of the formula VIII

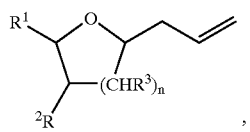

where $R^1$, $R^2$ and $R^3$, and n are as defined above, with a compound of the formula IX

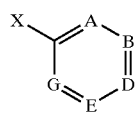

In this reaction, $R^1$, $R^2$ and $R^3$ may be present in protected or unprotected form, and A, B, D, E and G are as defined above. X is a halogen atom, and the bond between G and E can also be a single bond (i.e. IX is a 1,3-cyclohexadienyl derivative). The reaction proceeds under transition metal catalysis, where the transition metal preferably is palladium.

Following the coupling reaction, the reaction product may be transformed into the desired final product using methods that are well known to those skilled in the art of organic synthesis. Any protecting groups used in the coupling reaction may be removed by methods that are well known in the art. The compounds according to the present invention can be purified by well known methods, such as chromatography, recrystallization, etc.

The glycomimetics of the present invention are therefore useful in pharmaceuticals for therapy or prophylaxis of diseases associated with excessive selectin-mediated cell adhesion. These pharmaceuticals are particularly suitable for the treatment of acute and chronic inflammation that is characterized pathophysiologically by a disruption of cell circulation, for example of lymphocytes, monocytes and neutrophil granulocyte circulation. Such inflammation is found in: autoimmune diseases such as acute polyarthritis, rheumatoid arthritis and insulin-dependent diabetes mellitus (IDDM); acute and chronic transplant rejections; shock lung (ARDS, adult respiratory distress syndrome); inflammatory and allergic skin diseases, for example psoriasis and contact eczema; cardiovascular disorders such as myocardial infarct; reperfusion injuries after thrombolysis, angioplasty or by-pass operations; septic shock; and systemic shock. A further indication is the treatment of metastatic tumors, since tumor cells carry surface antigens possessing both sialyl-Lewis-X and sialyl-Lewis-A structures as recognition epitopes. It is also possible to use these pharmaceuticals, which are stable in the acidic medium of the stomach, for antiadhesive therapy of *Helicobacter pylori* and related microorganisms, alone or in combination with antibiotics. In addition, the pharmaceuticals may be used for therapy of the cerebral form of malaria.

The pharmaceuticals according to the invention may be administered intravenously, orally or parenterally or as implants, and rectal application is also possible. Suitable solid or liquid pharmaceutical preparation forms are well known in the art, and include, for example, granules, powders, plain tablets, film-coated tablets, (micro)capsules, suppositories, syrups, emulsions, suspensions, aerosols, drops and injectable solutions in ampule form. Formulations with protracted release of active compound may also be used. These formulations customarily are prepared using excipients and additives and/or auxiliaries such as disintegrants, binders, coating agents, swelling agents, glidants or lubricants, flavorings, sweeteners or solubilizers. Frequently used excipients or auxiliaries include magnesium carbonate, titanium dioxide, lactose, mannitol and other sugars, talc, lactoprotein, gelatin, starch, vitamins, cellulose and their derivatives, animal and vegetable oils, polyethylene glycols and solvents, for instance sterile water, alcohols, glycerol and polyhydric alcohols. The pharmaceutical preparations are preferably prepared and administered in dose units. Solid dose units are tablets, capsules and suppositories.

For patient treatment, different daily doses are required depending on the efficacy of the compound, the mode of application, the nature and severity of the disease and the age and body weight of the patient. Under certain circumstances, however, higher or lower daily doses may also be appropriate. Determination of an appropriate dosage regimen for a patient is routine for those skilled in the art of prescribing pharmaceuticals. The daily dose additionally may depend on the number of receptors expressed during the course of the disease. In the initial stage of the disease only a few receptors may be expressed on the cell surface and, accordingly, the daily administered dose is lower than in the case of patients who are severely ill. Once a daily dose is determined, it can be administered either in a single administration in the form of an individual dose unit, or in a number of small dose units, or by multiple administration of subdivided doses at defined intervals. The pharmaceuticals according to the invention are produced by bringing a compound according to the present invention into the or an appropriate administration form with customary excipients and, if desired, additives and/or auxiliaries.

Synthesis of Compounds of the Formula I

The synthesis of compounds of Formula I is illustrated below for the compound 8. Those skilled in the art will recognize that the synthetic scheme described below may be modified by methods that are well known in the art to provide all of the compounds corresponding to Formula I.

The synthesis of the pure α-C-glycoside 8 was carried out in only 3 stages with an overall yield of 72, by the reaction scheme shown below.

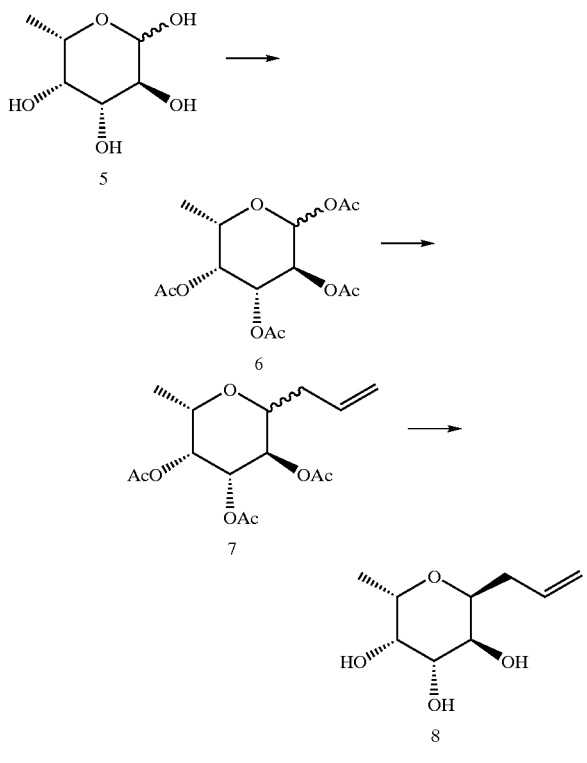

Thus, L-fucose 5 was acetylated with acetic anhydride/pyridine to provide the tetra acetate (95–98%), which was then treated, under BF$_3$ catalysis, with allylsilane. The resulting C-glycoside 7 (92%, α/β ratio 10:1), was quantitatively deacetylated, and purified by recrystallization. By appropriate choice of the recrystallization conditions it was possible to obtain the α derivative 8 in pure form, (i.e. without additional amounts of the corresponding β derivative), in contrast to known processes that failed to remove the contaminating β isomer. The recrystallization is the only purification step in this sequence.

The allyl side chain of the C-glycoside 8 can then be functionalized without introduction of additional protective groups. Alternatively, the perbenzylated compound 8a may be used for further derivatization.

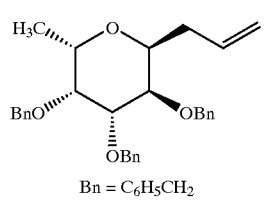

Bn = C$_6$H$_5$CH$_2$

A reaction that is particularly suitable for this derivatization is the transition metal-catalyzed C—C linkage of a protected or unprotected C-allyl glycoside (e.g. 8 or 8a) with a substituted or unsubstituted aryl or heteroaryl halide/triflate (the so-called Heck reaction, see e.g. Larock et al., *J. Org. Chem.* 56:2615 (1991). This reaction also may be carried out using a 1,3-cyclohexadienyl halide or triflate in the coupling reaction, as described below in Example 27, for example.

The preferred catalyst for this reaction is a Pd° compound. Examples of suitable catalysts include Pd(PPh$_3$)$_4$, Pd(OAc)$_2$, and Pd(dba)$_2$, where (dba) is dibenzylacetone. The catalyst may also be prepared in situ by addition of a reducing agent to a Pd$^{II}$ salt, for example by adding P(Ph)$_3$ to Pd(OAc)$_2$.

The synthesis generally leads in a few steps to the pharmacologically relevant end compound in good to very good yields. The products of the Heck reaction can frequently be isolated by extraction or reprecipitation without further purification by chromatography.

The double bond may also easily be used for further derivatization. Examples of suitable derivatizations include: hydrogenation; halogenation; Diels-Alder reactions; epoxidation (Jacobsen et al., *J. Am. Chem. Soc.* 112:2801 (1990)); and hydroxylation (Sharpless et al., *J. Am. Chem. Soc.* 116:1278 (1994). These and other functionalization reactions well known to the skilled artisan provide efficient and simple access to modified derivatives. For example, the Heck reaction of Boc-4-iodophenylalanine (BOC='butoxycarbonyl) with the allyl fucoside gives the corresponding neoglycoamino acid, which may be employed successfully both in solid-phase and liquid phase peptide synthesis for the preparation of modified peptides.

The reactions described above can be applied analogously to other C-glycoside units, for example compounds 9 and 9a, which can be prepared from D-mannose, or compounds 10 and 10a, which can be prepared from ribose.

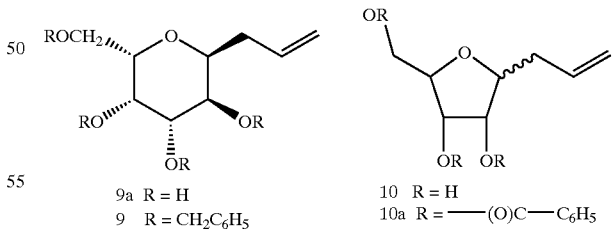

9a R = H
9  R = CH$_2$C$_6$H$_5$

10  R = H
10a R = ——(O)C——C$_6$H$_5$

The process according to the present invention can also be used to prepare, in corresponding fashion using techniques well known in the art, derivatives of L-galactose, L-rhamnose, and glucose.

Primary Assays to Investigate the Action of the Compounds According to the Present Invention on Cell Adhesion to Recombinant, Soluble Selectin Fusion Proteins.

To test the efficacy of the compounds according to the invention on the interaction between E- and P-selectins (former nomenclature ELAM-1 and GMP-140, respectively) with their ligands, assay that are specific for either E- or P-selectin interactions are used. In these assays, the ligands may be supplied in their natural form as surface structures on promyelocytic HL60 cells. Since HL60 cells contain ligands and adhesion molecules of very different specificity, the desired specificity of the assay must therefore be provided by the binding component. Preferably, the binding components used are recombinant, soluble, fusion proteins formed from the extracytoplasmatic domains of E- or P-selectin, respectively, and the constant region of human immunoglobulin of the IgG1 subclass. Preferably, a non-selectin binding fusion protein is used as a negative control. An example of a suitable negative control is a fusion protein formed between the extracytoplasmic domain of CD4 and the IgG constant region.

These fusion proteins are then used in a cell adhesion assay in which COS cells transfected with the recombinant fusion proteins are first bound to the surface of a microtiter plate. The compound to be tested is added to the wells of the microtiter platein varying concentrations, followed by HL60 cells. After a defined period of time, the wells of the microtiter plate are washed and the HL60 cells adhering to the plate are counted. In a preferred embodiment, the HL60 cells are prelabeled with a fluorescent dye to facilitate cell counting. The number of cells adhering to the plate allows quantification of the inhibitory properties of the compound under test. Methods for assaying cell adhesion inhibition are described in more detail infra.

Leukocyte Adhesion—Testing the Efficacy of the Novel Compounds in vivo

In inflammatory processes and other states which activate the cytokines, the destruction of tissue by inward migrating leukocytes or leukocytes which block the microcirculation plays a critical part. The first phase, which is critical for the subsequent disease process, is activation of leukocytes within the bloodstream, especially in the pre- and postcapillary region. The leukocytes leave the axial flow of the blood, and initially attach to the inner vascular wall, i.e. to the vascular endothelium. All subsequent leukocyte effects, i.e. the active migration through the vascular wall and the subsequent oriented migration in the tissue, are follow-on reactions (Harlan, *Blood* 65, 513–525, 1985).

This receptor-mediated interaction of leukocytes and endothelial cells is regarded as an initial sign of the inflammatory process. In addition to the adhesion molecules already physiologically expressed, under the action of inflammatory mediators (leukotrienes, platelet activating factor) and cytokines (TNF-alpha, interleukins), a temporally graded, massive expression of adhesion molecules takes place on the cells. They are at present divided into three groups: the immunoglobulin gene superfamily, the integrins, and the selecting. Whereas adhesion takes place between molecules of the Ig gene superfamily and the protein-protein bonds, lectin-carbohydrate bonds are predominant in the interaction of selectins (Springer, *Nature* 346:425 (1990); Hughes, *Scrips Magazine* 6:30 (1993); Springer, *Cell* 76:301 (1994)).

The present invention, thus generally described, will be understood more readily by reference to the following examples, which are provided by way of illustration and are not intended to be limiting of the present invention.

EXAMPLES

I. Preparation of Compounds of the Formula VIII and their use in Preparing C-glycosides

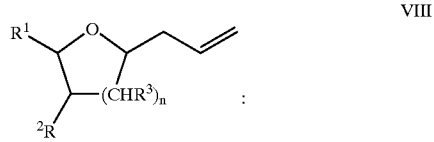

VIII

Example 1

Preparation of the C-glycoside Unit 8 (L-fucose Derivative)

L-Fucose (5) (250 g, 1.52 mol) was admixed with pyridine (616 ml, 7.62 mol) and acetic anhydride (633 ml, 6.7 mol) and the mixture was stirred at room temperature for 24 h. The solvent was removed on a rotary evaporator and the residue was dried under a high vacuum to provide 6 (496 g, 98%) as a yellow oil.

TLC [hexane/ethyl acetate: 1/1]: $R_f$=0.60.—$^1$H-NMR (300 MHZ, CDCl$_3$): δ=1.18 (d, 3H, $J_{6,5}$=6.9 Hz, 6-H$^{Fuc}$), 2.00–2.15 (4 s, 12H, CH$_3$).

Compound 6 (50 g, 0.15 mol) was dissolved in acetonitrile (300 ml) under argon and the solution was cooled to −10° C. Allylsilane (47.9 ml, 0.30 mol) and boron trifluoride—diethyl ether complex (20.4 ml, 0.166 mol) were added, and the mixture was stirred at −10° C. for 1 h. After warming to room temperature, stirring was continued for a further 3 h. The solution was poured into saturated sodium hydrogen carbonate solution and extracted with ethyl acetate. Solvent was removed on a rotary evaporator. The residue was taken up in dichloromethane and filtered through a short silica gel column. Removal of solvent gave 7 (α/β 10/1) as a yellow oil (43.5 g, 92%).

TLC [hexane/ethyl acetate: 1/1]: $R_f$=0.65.—$^1$H-NMR (300 MHZ, CDCl$_3$): δ=1.19 (d, 3H, $J_{6,5}$=6.9 Hz, 6-H$^{Fuc}$), 2.00–2.15 (3 s, 9H, CH$_3$), 2.20–2.58 (m, 2H), 3.98 (m, 1H), 4.28 (m, 1H), 5.05–5.85 (m, 6H).

The allyl derivative 7 (43.5 g, 0.139 mol) was dissolved in methanol (200 ml), and sodium methanolate solution (3 ml, 30% strength) was added. The solution was stirred at room temperature for 2 h and neutralized with acidic ion exchanger (Dowex® 50 W×8). The ion exchanger was filtered off and solvent was removed on a rotary evaporator. The deacetylated fucose derivative was obtained as a pale yellow solid (26.0 g, quantitative yield).

This residue was dissolved with heating in ethyl acetate and the solution was filtered while hot. Following removal of the solvent on a rotary evaporator, the residue was redissolved with heating in moist ethyl acetate. On cooling the solution, 8 crystallized out as a white solid (20.8 g, 80%).

TLC [dichloromethane/methanol: 10/1]: $R_f$=0.25.—$^1$H-NMR (300 MHZ, D$_2$O): δ=1.05 (d, 3H, $J_{6,5}$=6.9 Hz, 6-H$^{Fuc}$), 2.19–2.43 (m, 2H), 3.60–4.00 (m, 5H), 5.05 (m, 2H), 5.62–5.80 (m, 1H).

Under standard conditions (see Masamune et al., *Tetrahedron Lett.* 28:4303 (1987)) 8 was converted into the corresponding tribenzyl derivative 8a.

Example 2

Preparation of the C-glycoside Unit 9 (Mannose Derivative)

The mannose derivative 9 was prepared in analogy to 8 as an α/β mixture over 3 stages in 62% yield.

TLC [dichloromethane/methanol: 10/1]: $R_f$=0.30.—$^1$H-NMR (300 MHZ, $D_2O$): δ=2.19–2.43 (m, 2H), 3.60–4.00 (m, 7H), 5.05 (m, 2H), 5.62–5.80 (m, 1H).

Example 3

Preparation of the C-glycoside Unit 10a (Ribose Derivative)

1-O-Acetyl-2,3,5-tri-O-benzoyl-β-D-ribofuranose (1.0 g, 2.0 mmol) was dissolved in acetonitrile (10 ml) under argon and the solution was cooled to −10° C. Following addition of allylsilane (0.48 ml, 3.0 mmol) and boron trifluoride—diethyl ether complex (0.25 ml, 0.2 mmol), the mixture was stirred at −10° C. for 1 h. After warming to room temperature, stirring was continued for a further 2 h. The solution was poured into saturated sodium hydrogen carbonate solution and subjected to extraction with ethyl acetate. Solvent was removed on a rotary evaporator. The residue was taken up in dichloromethane and filtered through a short silica gel column. Removal of solvent under reduced pressure gave the allyl compound 10a (α/β 4/1) as a yellow oil (0.798 g, 76%).

TLC [hexane/ethyl acetate: 1/1]: $R_f$=0.60.—$^1$H-NMR (300 MHZ, $CDCl_3$): δ=2.51 (m, 2H), 4.20–6.05 (m, 8H), 7.10–8.35 (m, 15H).

II. Heck Reactions with Protected allyl-C-alycosides. Reactions of the Protected Compounds of the Formula VIII with Compounds of the Formula IX

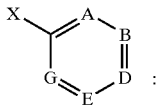

IX

Example 4

A mixture of 2,3,4-tri-O-benzyl-C-allyl-fucopyranoside 8a (200 mg, 0.436 mmol), iodobenzene (89 mg, 0.436 mmol) and sodium carbonate (69 mg, 0.651 mmol) in dimethylformamide was admixed under an argon atmosphere with $Pd(OAc)_2$ (3 mg, 3 mol %) and the mixture was stirred at a temperature of 70° C. for 16 h. The mixture was filtered and the solvent was removed under a high vacuum to give, following flash chromatography over silica gel with isohexane/ethyl acetate (10/1), 11 as a colorless oil (190 mg, 0.355 mmol, 81.5%).

TLC [hexane/ethyl acetate: 3/1]: $R_f$=0.56.—$^1$H-NMR (300 MHZ, $CDCl_3$): δ=1.32 (d, 3H, $J_{6,5}$ 6.9 Hz, 6-H$^{Fuc}$), 2.49 (m, 2H, α-$CH_2$), 3.83–3.86, 4.01, 4.12 (5H, 1-H$^{Fuc}$, 2-H$^{Fuc}$, 3-H$^{Fuc}$, 4-H$^{Fuc}$, 5-H$^{Fuc}$), 4.42–4.80 (6H, $CH_2$-Ph), 6.11 (dt, 1H, $J_{β,α}$=7.1, $J_{β,γ}$=15.8 Hz, β-H), 6.39 (d, 1H, $J_{γ,β}$=15.9 Hz, γ-H), 7.23–7.40 (20H, H—Ar); $^{13}$C-NMR (75.4 MHZ, $CDCl_3$): d=15.11 (6-C$^{Fuc}$), 31.96 (α-$CH_2$), 126.05–128.27, 128.34, 128.37, 128.40 (C—Ar), 131.72 (C-allyl), 137.62, 138.29, 138.59, 138.78 ($C_{quart.}$—Ar)

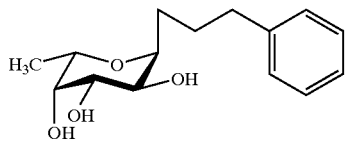

11

Example 5

A mixture of 2,3,4-tri-O-benzyl-C-allyl-fucopyranoside 8a (185 mg, 0.403 mmol), 4'-bromobenzo-18-crown-6 (189 mg, 0.484 mmol) and sodium carbonate (106 mg, 1 mmol) in dimethylformamide was admixed under an argon atmosphere with $Pd(OAc)_2$ (4.5 mg, 5 mol %) and the mixture was stirred at a temperature of 70° C. for 3 h. Following the addition of triphenylphosphine (21 mg, 20 mol %), stirring was continued at 100° C. for a further 6 h, after which the mixture was filtered and the solvent was removed under a high vacuum. Flash chromatography over silica gel using dichloromethane/methanol (15/1) gave 12 as an amorphous solid (206 mg, 0.268 mmol, 66.5%).

TLC [dichloromethane/methanol: 10/1]: $R_f$=0.25.—$^1$H-NMR (300 MHZ, $CDCl_3$): δ=1.32 (d, 3H, $J_{6,5}$=6.7 Hz, 6-H$^{Fuc}$), 2.46 (m, 2H, α-$CH_2$), 3.6–3.9 (m, H-crown-6), 3.6–4.2 (5H, 1-H$^{Fuc}$, 2-H$^{Fuc}$, 3-H$^{Fuc}$, 4-H$^{Fuc}$, 5-H$^{Fuc}$) 4.44–4.80 (6H, $CH_2$-Ph), 5.98 (dt, 1H, $J_{β,α}$=7., $J_{β,γ}$=16 Hz, β-H), 6.30 (d, 1H, $J_{β,γ}$=16 Hz, γ-H), 6.9–7.40 (18H, H—Ar).

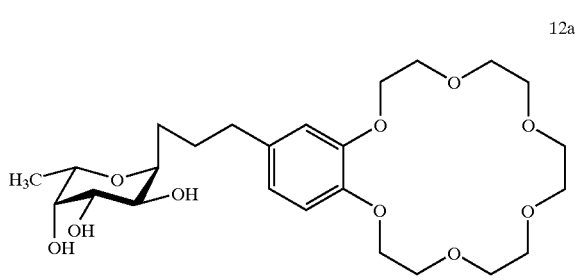

12a

Example 6

A solution of 12 (153 mg, 0.199 mmol) in a mixture of methanol/dioxane/AcOH (10:1:1, 10 ml) was admixed with Pd/C (10% Pd on active charcoal, 100 mg) and hydrogenated under a hydrogen atmosphere for 16 h. The mixture was admixed with 20 ml of methanol and filtered through a sterile syringe filter (0.2 mm, Schleicher & Schuell) and the solution was concentrated in vacuo. Exclusion chromatography on Sephadex LH20 with methanol as eluent provided 12a (87 mg, 0.173 mmol, 87%) as an amorphous solid.

TLC [butanol/acetic acid/water: 3/1/1]: $R_f$=0.17.—$^1$H-NMR (300 MHZ, $CD_3OD$): δ=1.23 (d, 3H, $J_{6,5}$=6.6 Hz, 6-H$^{Fuc}$), 1.64 (m, 4H, β,γ-$CH_2$), 2.63 (m, 2H, α-$CH_2$), 3.67, 3.88, 4.14 (m, H-crown-6, 1-H$^{Fuc}$, 2-H$^{Fuc}$, 3-H$^{Fuc}$, 4-H$^{Fuc}$, 5-H$^{Fuc}$), 6.94–6.72 (18H, H—Ar)

Example 7

A solution of 2,3,4-tri-O-benzyl-C-allyl-fucopyranoside 8a (100 mg, 0.218 mmol), 4-iodoanisole (51 mg, 0.218 mmol) and triethylamine (44.1 mg, 0.436 mmol) in dimethylformamide was admixed under an argon atmosphere with $Pd(OAc)_2$ (3 mg, 3 mol %). The mixture was stirred at a temperature of 100° C. for 16 h and then was filtered, and the solvent removed under a high vacuum. Flash chromatography on silica gel with isohexane/ethyl acetate (8/1) provided 13 as a colorless oil (45 mg, 0.08 mmol, 36.6%).

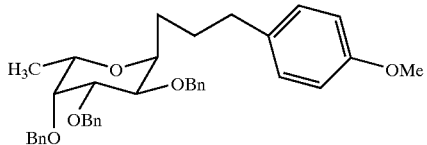

13

TLC [hexane/ethyl acetate: 4/1]: $R_f$=0.36.—$^1$H-NMR (300 MHZ, CDCl$_3$): δ=1.31 (d, 3H, $J_{6,5}$=6.6 Hz, 6-H$^{Fuc}$), 2.47 (m, 2H, α-CH$_2$), 3.80, 4.01, 4.10 (5H, 1-H$^{Fuc}$, 2-H$^{Fuc}$, 3-H$^{Fuc}$, 4-H$^{Fuc}$, 5-H$^{Fuc}$), 3.81 (s, 3H, OCH$_3$), 4.42–4.80 (6H, CH$_2$-Ph), 5.96 (dt, 1H, $J_{b,a}$=7.1, $J_{b,g}$=15.8 Hz, β-H), 6.34 (d, 1H, $J_{γ,β}$=15.8 Hz, γ-H), 6.88 (d, 2H, $J_{Ar}$=8.9 Hz, Ar), 7.22 (d, 2H, $J_{Ar}$=8.9 Hz, Ar), 7.24–7.40 (15H, H—Ar).

Example 8

A solution of 13 (31 mg, 0.055 mmol) in methanol/formic acid (10 ml/5 ml) was admixed with palladium black (200 mg). After 16 h the mixture was filtered and the solution was concentrated in vacuo. Exclusion chromatography on Biogel P2 provided 14 (15 mg, 0.05 mmol, 91%) as an amorphous solid.

$^1$H-NMR (300 MHZ, CD$_3$OD): δ=1.23 (d, 3H. $J_{6,5}$=6.6 Hz, 6-H$^{Fuc}$), 1.64 (m, 4H, β,γ-CH$_2$), 2.63 (m, 2H, α-CH$_2$), 6.9–7.3(4H, H—Ar).

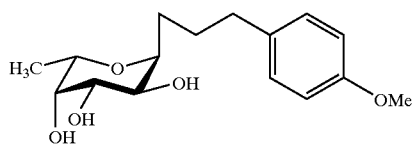

14

Example 9

A mixture of 2,3,4-tri-O-benzyl-C-allyl-fucopyranoside 8a (250 mg, 0.545 mmol), ethyl 4-bromobenzoate (137 mg, 0.6 mmol) and sodium carbonate (116 mg, 1.09 mmol) in dimethylformamide (10 ml) was admixed under an argon atmosphere with Pd(OAc)$_2$ (3.7 mg, 3 mol %). The mixture was stirred at a temperature of 100° C. for 24 h and then filtered. Solvent was removed under a high vacuum to give, following flash chromatography on silica gel with dichloromethane/methanol (8/1), 15 as an amorphous solid (284 mg, 0.468 mmol, 85.9%)

TLC [hexane/ethyl acetate: 3/1]: $R_f$=0.34.

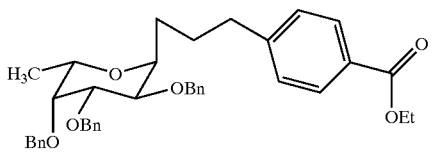

15

Example 10

A solution of 15 (242 mg, 0.399 mmol) in methanol/dioxane/formic acid (10 ml/1 ml/1 ml) was admixed with palladium black (200 mg). The mixture was filtered after 24 h, solvent was removed in vacuo and the residue dissolved in methanol/water/1 M NaOH (4 ml:4 ml:3 ml). Neutralization with Amberlite IR 120, filtration and exclusion chromatography on Sephadex® LH20 using methanol as eluent gave 16 (120 mg, 0.387 mmol, 97%) as an amorphous solid.

TLC [RP 18, water/methanol: 1/1]: $R_f$=0.30.—$^1$H-NMR (300 MHZ, CDCl$_3$): δ=1.14 (d, 3H, $J_{6,5}$=6.4 Hz, 6-H$^{Fuc}$), 1.52 (β- or γ-CH$_2$), 1.68 (α-CH$_2$), 2.62–2.83 (β- or γ-CH$_2$), 3.64–3.73 (3-H$^{Fuc}$, 4-H$^{Fuc}$, 5-H$^{Fuc}$), 3.92 (2-H$^{Fuc}$), 3.98 (1-H$^{Fuc}$), 7.35 (d, 1H, $J_{Ar}$=8 Hz, H—Ar), 7.84 (d, 1H, $J_{Ar}$=8 Hz, H—Ar); $^{13}$C-NMR (75.4 MHZ, CDCl$_3$): δ=18.4 (6-C$^{Fuc}$), 25.5, 29.5, 37.4 (α-C, β-C, γ-C), 69.5 (3-C$^{Fuc}$ or 4-C$^{Fuc}$ or 5-C$^{Fuc}$), 70.9 (2-C$^{Fuc}$), 72.7 (3-C$^{Fuc}$ or 4-C$^{Fuc}$ or 5-C$^{Fuc}$), 74.6 (3-C$^{Fuc}$ or 4-C$^{Fuc}$ or 5-C$^{Fuc}$), 78.4 (1-C$^{Fuc}$), 131.2, 132 (C—Ar), 136.5, 149.2 (C$_{quart.}$ —Ar), 178.2 (C=O)

Example 11

Diethyl aminomalonate (17.2 mg, 0.081 mmol) and 16 (18 mg, 0.058 mmol) were dissolved in dimethylformamide. The mixture was cooled to 0° C., N-(3-dimethylaminopropyl)-N'-ethylcarbodiimide hydrochloride was added, and the mixture was stirred at 0° C. for 1 h followed by warming to room temperature over the course of 2 h. Solvent was removed in vacuo and the residue was purified by flash chromatography on silica gel using dichloromethane/methanol (10/1) as eluent. 17 (23 mg, 0.0492 mmol, 84.8%) was obtained as an amorphous solid.

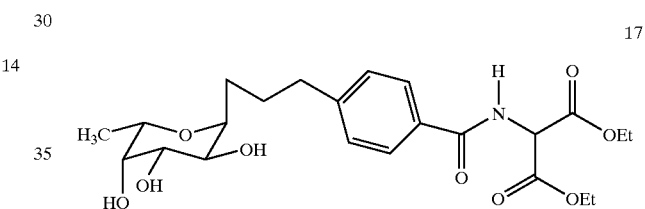

17

TLC [dichloromethane/methanol: 10/1]: $R_f$=0.18.—$^1$H-NMR (300 MHZ, CD$_3$OD): δ=1.10 (d, 3H, $J_{6,5}$=6.4 Hz, 6-H$^{Fuc}$), 1.20 (dd, 6H, J=7.3 Hz, CH$_3$), 1.53, 1.65, 2.62 (α-CH$_2$, β-CH$_2$, γ-CH$_2$), 3.45–4.28 (2-H$^{Fuc}$, 3-H$^{Fuc}$, 4-H$^{Fuc}$, 5-H$^{Fuc}$), 4.17 (m, 4H, CH$_2$), 7.23 (d, 1H, $J_{Ar}$=8.2 Hz, H—Ar), 7.70 (d, 1H, $J_{Ar}$=8.2 Hz, H—Ar).

Example 12

Compound 17 (19 mg, 0.0406 mmol) was hydrolyzed in methanol/1 M NaOH (1 ml: 3 ml) over the course of 2 h. Neutralization with Amberlite IR 120, filtration and exclusion chromatography on Biogel P2 using water as eluent gave 18 (15 mg, 0.037 mmol, 91%) as an amorphous solid.

TLC [butanol/acetic acid/water: 3/1/1]: $R_f$=0.31.—$^1$H-NMR (300 MHZ, D$_2$O): δ=1.08 (d, 3H, $J_{6,5}$=6.7 Hz, 6-H$^{Fuc}$), 1.34–1.7, 2.59–2.77 (α-CH$_2$, β-CH$_2$, γ-CH$_2$), 3.63–3.66, 3.82–3.94 (1-H$^{Fuc}$, 2-H$_{Fuc}$, 3-H$^{Fuc}$, 4-H$^{Fuc}$, 5-H$^{Fuc}$) 7.35 (d, 1H. $J_{Ar}$=8.3 Hz, H—Ar), 7.73 (d, 1H, $J_{Ar}$=8 Hz, H—Ar)

Example 13

A mixture of 2,3,4-tri-O-benzyl-C-allyl-fucopyranoside (4.34 g, 9.46 mmol), Boc-4-iodo-phenylalanine (4.47 g, 11.36 mmol) and sodium carbonate (6.02 g, 56.76 mmol) in dimethylformamide (40 ml) was admixed under an argon atmosphere with Pd(dba)$_2$ (dba=dibenzylacetone) (3 mol %). The mixture was stirred at a temperature of 75° C. for 6 h and then filtered. Solvent was removed under a high vacuum, and exclusion chromatography on Sephadex LH20 using methanol as eluent gave 19 as an amorphous solid (5.25 g, 7.26 mmol, 76.7%).

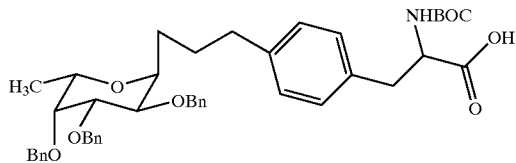

19

TLC [dichloromethane/methanol: 10/1]: $R_f$=0.21.—$^1$H-NMR (300 MHZ, DMSO): δ=1.23 (d, 3H, $J_{6,5}$=6.5 Hz, 6-H$^{Fuc}$), 1.39 (s, 9H, H$^{Boc}$), 2.48 (m, 2H, α-CH$_2$), 2.96 (dd, 1H, $J_{β,α}$=5, $J_{β,β}$=14 Hz, b$_α$-H$^{Phe}$), 3.08(dd, 1H, $J_{β,α}$=5, $J_{β,β}$=14 Hz, b$_β$-H$^{Phe}$), 3.65–4.1 (6H, 1-H$^{Fuc}$, 2-H$^{Fuc}$, 3-H$^{Fuc}$, 4-H$^{Fuc}$, 5-H$^{Fuc}$, α-H$^{Phe}$), 4.46–4.79 (6H, CH$_2$-Ph), 5.83 (d, 1H, $J_{NH,α}$=6 Hz, HN$^{Phe}$), 6.13 (dt, 1H, $J_{β,α}$=7, $J_{β,γ}$=16 Hz, β-H), 6.41 (d, 1H, $J_{γ,β}$=16 Hz, γ-H), 7.09 (d, 2H, $J_{Ar}$=8 Hz, Ar), 7.20 (d, 2H, $J_{Ar}$=8 Hz, Ar), 7.30–7.45 (15H, H—Ar).

Example 14

19 (155 mg, 0.214 mmol) was admixed with trifluoroacetic acid (20 ml, 95%) and the mixture was stirred for 1 h. Following removal of the solvent in vacuo, the residue was dissolved in methanol:dioxane: acetic acid (15 ml/3 ml/3 ml), Pd/C (10% Pd on active charcoal, 110 mg) was added to the solution and the mixture was hydrogenated under a hydrogen atmosphere for 16 h. The mixture was diluted with methanol (20 ml), and filtered and concentrated in vacuo. Exclusion chromatography on Biogel P2 using water as eluent provided 20 (60 mg, 0.17 mmol, 79.2%) as an amorphous solid.

TLC [butanol/acetic acid/water: 3/1/1]: $R_f$=0.34.—$^1$H-NMR (300 MHZ, D$_2$O): δ=1.03 (d, 3H, $J_{6,5}$=6.5 Hz, 6-H$^{Fuc}$), 1.50–1.55 (α-CH$_2$, β- or γ-CH$_2$), 2.59 (β- or γ-CH$_2$), 2.91 (dd, 1H, $J_{β,α}$=8.3, $J_{β,β}$=14.3 Hz, b$_α$-H$^{Phe}$), 3.20 (dd, 1H, $J_{β,α}$=4.3, $J_{β,β}$=14.4 Hz, b$_β$-H$^{Phe}$), 3.45–3.70 (6H, 1-H$^{Fuc}$, 2-H$^{Fuc}$, 3-H$^{Fuc}$, 4-H$^{Fuc}$, 5-H$^{Fuc}$, α-H$^{Phe}$), 7.03 (d, 2H, $J_{Ar}$=8.1 Hz, Ar), 7.11 (d, 2H, $J_{Ar}$=8.1 Hz, Ar); $^{13}$C-NMR (75.4 MHZ, D$_2$O): δ=16.1 ($_6$-C$^{Fuc}$), 24.9, 27.8, 34.8 (α-C, β-C, γ-C), 36.8, 55.6, 67.5, 68.7, 70, 70.9, 72.9 (1-C$^{Fuc}$, 2-C$^{Fuc}$, 3-C$^{Fuc}$, 4-C$^{Fuc}$, 5-C$^{Fuc}$), 128.2, 129.2 (C—Ar), 134.9, 140.5 (C$_{quart.}$—Ar), 170.1 (C=O).

Example 15

A mixture of 2,3,5-tri-O-benzoyl-C-allylriboside 10a (100 mg), p-iodobenzoic acid (1.5 equivalents) and sodium carbonate (3 equivalents) in dimethylformamide (5 ml) was admixed under an argon atmosphere with Pd(OAc)$_2$ (3 mol %) and the mixture was stirred at a temperature of 75° C. for 48 h. Solvent was removed under a high vacuum, the residue was dissolved in a little methanol, and 5 ml of sodium methanolate in methanol was added. The mixture was stirred for 1 h, and then neutralized with acidic ion exchanger Amberlite IR 120 to give, after flash chromatography on silica gel with dichloromethane: methanol (5:1), 21 as an amorphous solid (25 mg). TLC [dichloromethane/methanol: 2/1]: $R_f$=0.3.

Example 16

A mixture of 2,3,4-tri-O-benzyl-C-allylmannoside 9 (500 mg, 1.34 mmol), p-iodobenzoic acid (432 mg, 1.74 mmol) and sodium carbonate (222 mg, 2.68 mmol) in dimethylformamide (10 ml) was admixed under an argon atmosphere with Pd(OAc)$_2$ (3 mol %) and stirred at a temperature of 80° C. for 48 h. Solvent was removed under a high vacuum to give, after flash chromatography on silica gel with dichloromethane:methanol (15:1), 22 as an amorphous solid (390 mg, 59%).

TLC [dichloromethane/methanol: 20/1]: $R_f$=0.15.—$^1$H-NMR (300 MHZ, CD$_3$OD): δ=1.89, 2.02, 2.07, 2.10 (s, 12H, OAc), 2.60, 2.74 (m, 2H, α-CH$_2$), 4.0–4.4 (4H, 1-H$^{Man}$, 5-H$^{Man}$, 6-H$^{Man}$), 5.16, 5.25, 5.36 (3H, 2-H$^{Fuc}$, 3-H$^{Fuc}$, 4-H$^{Fuc}$), 6.38 (1H, β-H), 6.61 (d, 1H, $J_{γ,β}$=16 Hz, γ-H), 7.48 (d, 2H, H—Ar), 7.95 (d, 2H, H—Ar).

Catalytic hydrogenation of 22 in analogy to Example 14 provided the deprotected compound 22a.

III. Heck Reactions with Unprotected allyl-C-glycosides, Reactions of the Unprotected Compounds of the formula VIII with compounds of the formula IX

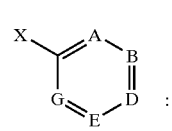

IX

Example 17

A mixture of C-allylfucopyranoside 8 (3 g, 15.94 mmol), 3-iodobenzoic acid (4.74 g, 19.13 mmol) and sodium carbonate (5.07 g, 47.82 mmol) in dimethylformamide (20 ml) was admixed under an argon atmosphere, after degassing three times, with Pd(OAc)$_2$ (107 mg, 3 mol %). The temperature was raised over the course of 3 h from 50° C. to 70° C., after which the mixture was filtered through kieselguhr and the solvent was removed in vacuo. The residue was taken up in a little water, filtered through a sterile syringe filter (0.2 mm, Schleicher & Schuell) and finally purified by exclusion chromatography on Biogel® P2 using water as eluent. Reprecipitation from water with acetone yielded 29 as an amorphous solid (4.64 g, 15.04 mmol, 94.4%).

TLC [dichloromethane/methanol: 10/1]: $R_f$=0.49.—$^1$H-NMR (300 MHZ, D$_2$O): δ=(d, 3H, $J_{6,5}$=6.4 Hz, 6-H$^{Fuc}$), 2.32 (m, 2H, α-CH$_2$), 3.53–3.97 (5H, 1-H$^{Fuc}$, 2-H$^{Fuc}$, 3-H$^{Fuc}$, 4-H$^{Fuc}$, 5-H$^{Fuc}$), 6.08 (dt, 1H, $J_{β,α}$=7, $J_{β,γ}$=15.7 Hz, β-H), 6.37 (d, 1H, $J_{γ,β}$=15.7 Hz, γ-H), 7.26 (dd, 1H, $J_{Ar}$=7.7 Hz, Ar), 7.37 (d, 1H, $J_{Ar}$=7.7 Hz, Ar), 7.59 (d, 1H, $J_{Ar}$=7.6 Hz, Ar), 7.75 (s, 1H, Ar).

Example 18

A mixture of C-allylfucopyranoside 8 (380 mg, 2.02 mmol), dimethyl 4-bromobenzylmalonate (608 mg, 2.02 mmol) and sodium carbonate (642 mg, 6.06 mmol) in dimethylformamide (10 ml) was admixed with Pd(OAc)$_2$ (3 mol %). The mixture was stirred for 4 h, gradually heating from 40° C. to 80° C. The mixture was stirred overnight at room temperature and filtered, and the solvent was removed in vacuo. The residue was hydrolyzed in methanol/1 M NaOH (1 ml: 3 ml) over the course of 1.5 h. Neutralization with Amberlite IR 120, filtration through a sterile syringe filter (0.2 mm, Schleicher & Schuell) and exclusion chromatography on Biogel® P2 with water as eluent gave 24 as an amorphous solid (305 mg, 0.802 mmol, 39.7%).

$^1$H-NMR (300 MHZ, D$_2$O): δ=1.23 (d, 3H, $J_{6,5}$=6.5 Hz, 6-H$^{Fuc}$), 2.60 (m, 2H, α-CH$_2$), 3.82–4.28 (5H, 1-H$^{Fuc}$, 2-H$^{Fuc}$, 3-H$^{Fuc}$, 4-H$^{Fuc}$, 5-H$^{Fuc}$), 6.39 (ddd, 1H, $J_{β,α}$=6.5, $J_{β,γ}$=15. Hz, β-H), 6.62 (d, 1H, $J_{g,b}$=15 Hz, γ-H), 7.34 (dd, 2H, $J_{Ar}$=8 Hz, Ar), 7.48 (d, 2H, $J_{Ar}$=8 Hz, Ar).

Example 19

A mixture of C-allylfucopyranoside 8 (330 mg, 1.75 mmol), p-bromobenzylbarbituric acid (520 mg, 1.75 mmol) and sodium carbonate (556 mg, 5.25 mmol) in dimethylformamide (10 ml) was admixed under an argon atmosphere with Pd(OAc)$_2$ (3 mol %). The mixture was stirred at a temperature of 40° C.→75° C. for 4 h. The mixture was filtered, the solvent was removed in vacuo, and exclusion chromatography on Biogel® P2 with water as eluent gave 25 as an amorphous solid (560 mg, 1.49 mmol, 85%).

TLC [dichloromethane/methanol: 2/1]: R$_f$=0.18.—$^1$H-NMR (300 MHZ, D$_2$O): δ=0.99 (d, 3H, J$_{6,5}$=6.6 Hz, 6-H$^{Fuc}$), 2.35 (m, 2H, α-CH$_2$), 3.54–4.0 (5H, 1-H$^{Fuc}$, 2-H$^{Fuc}$, 3-H$^{Fuc}$, 4-H$^{Fuc}$, 5-H$^{Fuc}$), 6 (ddd, 1H, J$_{β,α}$=7, J$_{β,γ}$=16 Hz, β-H), 6.33 (d, 1H, J$_{γ,β}$=16 Hz, γ-H), 7.05 (dd, 2H, J$_{Ar}$=8 Hz, Ar), 7.18 (d, 2H, J$_{Ar}$=8 Hz, Ar); $^{13}$C-NMR (75.4 MHZ, D$_2$O): δ=15.5 (6-C$^{Fuc}$), 27.3, 27.8, 66.9, 67.9, 69.8, 71.8, 75.4, 89.0, 125.9, 128.1 (C—Ar), 131.8, 134.7, 141.4, 153.1, 166.4.

Example 20

A mixture of C-allylfucopyranoside 8 (200 mg, 1.063 mmol), 5-bromonicotinic acid (215 mg, 1.063 mmol) and sodium carbonate (450 mg, 4.25 mmol) in dimethylformamide (4 ml) was admixed under an argon atmosphere with Pd(OAc)$_2$/triphenylphosphine (3 mol %). The mixture was stirred at a temperature of 50° C. for 4 h. Following the addition of 6 ml of ethylene glycol, the temperature was raised to 170° C. and the suspension was stirred for 4 h. The solvent was removed in vacuo to give, after exclusion chromatography on Biogel® P2 with water as eluent, 26 as an amorphous solid (93 mg, 0.301 mmol, 28%).

TLC [dichloromethane/methanol: 2/1]: R$_f$=0.28.—$^1$H-NMR (300 MHZ, D$_2$O): δ=1.0 (d, 3H, J$_{6,5}$=6.4 Hz, 6-H$^{Fuc}$), 1.38–1.61 (m, 4H, β- or γ-CH$_2$, α-CH$_2$), 2.50–2.66 (β- or γ-CH$_2$), 3.44–3.89 (1-H$^{Fuc}$, 2-H$^{Fuc}$, 3-H$^{Fuc}$, 4-H$^{Fuc}$, 5-H$^{Fuc}$), 7.92–8.89 (d, 1H, J$_{Ar}$=8 Hz, H—Ar), 7.84 (H—Ar); $^{13}$C-NMR (75.4 MHZ, CDCl$_3$): δ=15.6 (6-C$^{Fuc}$), 22.5, 26.3, 31.7 (α-C, β-C, γ-C), 66.7, 68.0, 69.8, 71.5 (2-C$^{Fuc}$, 3-C$^{Fuc}$, 4-C$^{Fuc}$, 5-C$^{Fuc}$), 75.4 (1-C$^{Fuc}$)

Example 21

A solution of 23, 24, 25 or 26 (100–200 mg) in methanol (5–10 ml) was admixed with Pd/C (10% Pd on active charcoal, 100 mg) and the mixture was hydrogenated under a hydrogen atmosphere for 2–20 h. The mixture was filtered through a sterile syringe filter (0.2 mm, Schleicher & Schuell) and the solution was concentrated in vacuo. Exclusion chromatography on Biogel® P2 with water as eluent provided the products with a hydrogenated double bond in essentially quantitative yields.

Example 22

A mixture of C-allylfucopyranoside 8 (300 mg, 1.6 mmol), p-iodoaniline (525 mg, 2.4 mmol) and sodium carbonate (398 mg, 4.8 mmol) in dimethylformamide (5 ml) was admixed under an argon atmosphere, after degassing three times, with Pd acetate (2 mol %). The temperature was raised to 80° C. over the course of 3 h, the mixture was then filtered through kieselguhr and the solvent was removed in vacuo. The residue was taken up in a little water, filtered through a sterile syringe filter (0.2 μm, Schleicher & Schuell) and finally purified on RP18 with methanol/water as eluent. Reprecipitation from water with acetone yields 27 as an amorphous solid (236 mg, 0.85 mmol, 53%).

$^1$H-NMR (300 MHZ, D$_2$O): δ=1.0 (d, 3H, J$_{6,5}$=6 Hz, 6-H$^{Fuc}$), 2.3 (m, 2H, α-CH$_2$), 3.5–4.1 (5H, 1-H$^{Fuc}$, 2-H$^{Fuc}$, 3-H$^{Fuc}$, 4-H$^{Fuc}$, 5-H$^{Fuc}$), 6.0 (dt, 1H, β-H), 6.4 (d, 1H, γ-H), 7.2 (m, 4H, Ar).

Example 23

The following compounds were reacted in the same manner as in Example 17 with the C-allylfucopyranoside 8.

a) o-bromophenylacetic acid gave 28, m-bromophenylacetic acid gave 28a,
b) ethyl m-bromobenzoate gave 29,
c) o-iodoaniline gave 30,
d) 5-bromo-3-indolylacetic acid gave 31,
e) 4-(4-bromophenyl)-4-hydroxypiperidine gave 32.

Example 24

A solution of p-[Boc-N-phenylalanine]-C-allyl-fucopyranoside (200 mg) in 5 ml of DMF was admixed in rapid succession with ethyl 4-piperidinecarboxylate (88 ml), HOBT (hydroxybenzotriazole) (89 mg), HBTU (hydroxybenzotriazoletetramethyluronium hexafluorophosphate) and DIPEA diisopropylethylamine) (115 ml). After 3 h the solvents were removed in vacuo. TLC [dichloromethane:methanol: 5/1]: R$_f$=0.52. The residue was dissolved in methanol, and then 20 ml of water were added to the solution and the mixture was finally hydrolyzed with sodium hydroxide solution at pH 11.5–12 to give 33. TLC [dichloromethane/methanol: 5/1]: R$_f$=0.17

Example 25

A solution of o-phenylacetic acid C-allyl-fucopyranoside (100 mg) in 5 ml of DMF was admixed in rapid succession with ethyl 4-piperidinecarboxylate (60 μl), HBTU (171 mg) and DIPEA (81 μl). After 4 h the solvents were removed in vacuo. TLC [dichloromethane: methanol: 5/1]: R$_f$=0.56. The residue was dissolved in methanol (5 ml) and then hydrolyzed with sodium hydroxide solution (10 ml, 1N) to give 34.

Example 26

A tetrapeptide having the sequence RGDS was synthesized by means of Fmoc solid-phase strategy on acid-labile TCP resin (Barlos et al., Tetrahedron Lett. 30:394 (1989)) The protected resin bound-peptide had the structure (TCP-Ser(OtBu)-Asp(OtBu)-Gly-Arg(Pmc)-Fmoc).

Solid-phase peptide synthesis on TCP resin used 20% piperidine in DMF and 3 equivalents of temporarily blocked amino acid, and HBTU/HOBT/DIPEA (3 equivalents of each). First, the N-terminal Fmoc protecting group was deblocked with 20% piperidine in DMF. The resin (2.6 g, 1 mmol) with the partially protected tetrapeptide was suspended in 20 ml and admixed in rapid succession with p-[Boc-N-phenylalanine]-C-allylfucopyranoside (541 mg), HOBT (163 mg), HBTU (456 mg) and DIPEA (209 μl). After washing with DMF, the resin was treated for 3 h with trifluoroacetic acid (5% water). Solvent was removed in vacuo and 35 (344 mg) was obtained after column chromatography on RP18 with water/methanol as eluent.

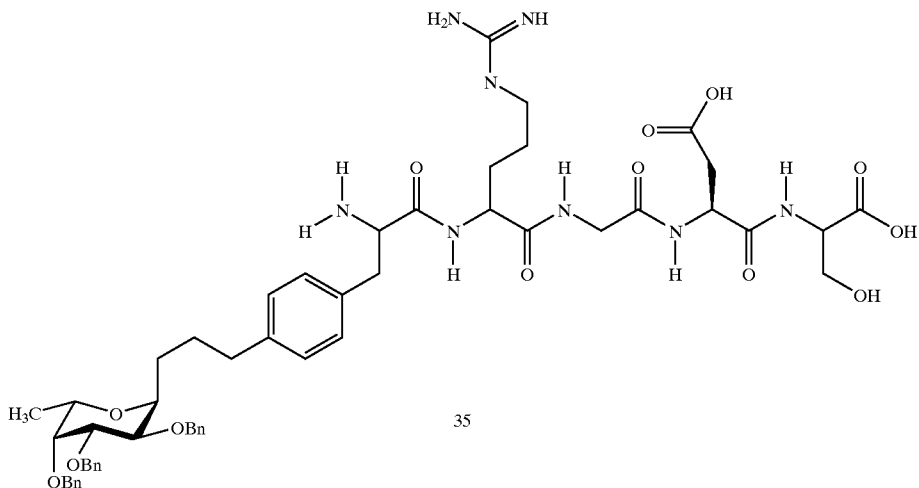

35

[dichloromethane/methanol: 2/1]: $R_f$=0.6.—$^1$H-NMR (300 MHZ, D$_2$O): δ=1.15 (d, 3H, $J_{6,5}$=6.4 Hz, 6-H$^{Fuc}$), 2.6 (m, 2H, α-CH$_2$), 3.7–4.3 (6H, 1-H$^{Fuc}$, 2-H$^{Fuc}$, 3-h$^{Fuc}$, 4-H$^{Fuc}$, 5-H$^{Fuc}$, α-H$^{Phe}$), 6.03 (m, 1H, Hz, β-H), 6.57 (d, 1H, $J_{γ,β}$=15.8 Hz, γ-H), 7.25 (d, 2H Ar), 7.43 (d, 2 H Ar); $^{13}$C-NMR (100.6 MHZ, D$_2$O): δ=18.0 (6 -C$^{Fuc}$), 171.1, 173.3, 174.7, 175.3, 177.6, 178.5 (C=O).

Subsequent hydrogenation of 35 (150 mg) for 3 h in methanol/AcOH (10 ml:10 ml) with 100 mg of Pd/C under a hydrogen atmosphere provided 36 (Ser-Asp-Gly-Arg-[C-FucPhe]) (143 mg), after filtration and concentration in vacuo.

TLC [dichloromethane/methanol: 2/1]: $R_f$=0.59.—$^1$H-NMR (300 MHZ, D$_2$O): δ=1.16 (d, 3H, $J_{6,5}$=6.2 Hz, 6-H$^{Fuc}$), 2.6 (m, 2H, α-CH$_2$), 3.65–4.1 (6H, 1-H$^{Fuc}$, 2-H$^{Fuc}$, 3-H$^{Fuc}$, 4-H$^{Fuc}$, 5-H$^{Fuc}$, α-H$^{Phe}$), 7.25 (m, 4H Ar); $^{13}$C-NMR (100.6 MHZ, D$_2$O): δ=17.9 (6-C$^{Fuc}$), 171.4, 173.2, 174.5, 175.4, 177.4, 177.9 (C=O)

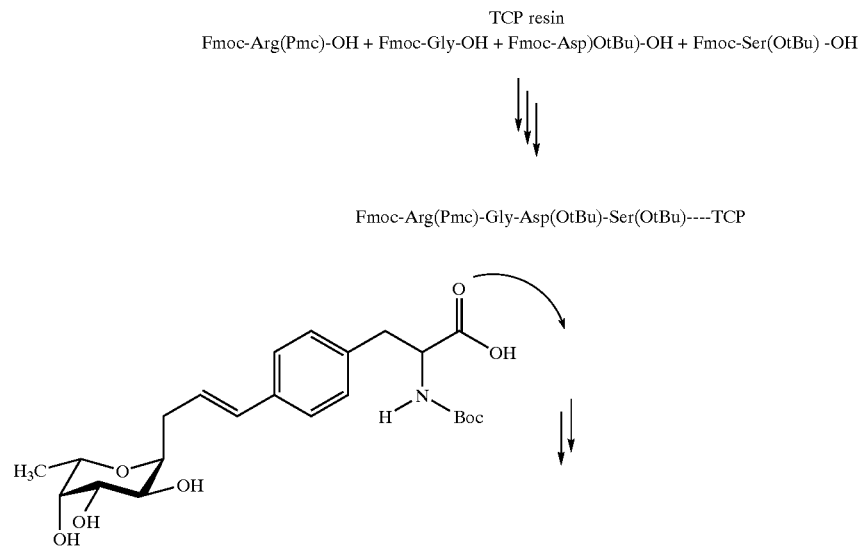

-continued

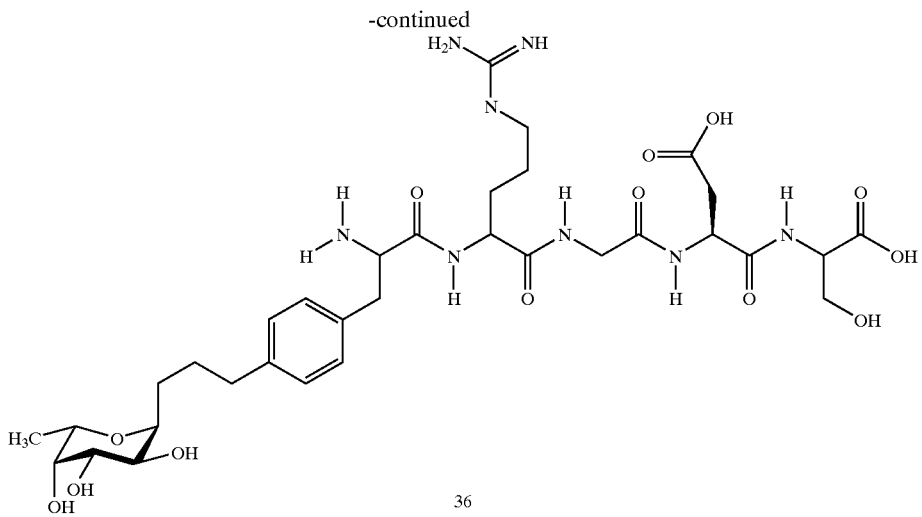

36

Example 27

A mixture of C-allylfucopyranoside 8 (1.422 g, 7.55 mmol), (2R,3R)-4-bromo-1-carboxy-2,3-dihydroxy-cyclohexa-4,6-diene (2.660 g, 11.32 mmol, available from Janssen) and sodium hydrogen carbonate (1.898 g, 22.6 mmol) in dimethylformamide (50 ml) was admixed under an argon atmosphere with Pd(OAc)$_2$ (85 mg, 5 mol %) and the mixture was stirred at a temperature of 60° C. for 1.5 h. The solids were filtered off, solvent was removed in vacuo, and the solid which remained was taken up in a little methanol and purified over a short column of silica gel with dichloromethane/methanol (1:3) as eluent. Medium-pressure chromatography on Bakerground RP18 with water/methanol (9:1→5:1 in 40 min, 5:1→1:9 in 17 min) as eluant provided 37 as an amorphous solid (1.847 g, 71%).

TLC [butanol/acetic acid/water: 3/1/1]: $R_f$=0.66.—$^1$H-NMR (300 MHZ, D$_2$O): d=1.07 (d, 3H, $J_{6,5}$=6.21 Hz, 6-H$^{Fuc}$); 1.54–1.61, 2.59–2.64 (m, 6H, α-CH$_2$, β-CH$_2$, γ-CH$_2$), 3.50–3.95 (2-H$^{Fuc}$, 3-H$^{Fuc}$, 4-H$^{Fuc}$, 5-H$^{Fuc}$, 1-H$^{Fuc}$), 6.70 (d, 1H, J=7 Hz, Ar), 7.31 (d, 1H, J=7 Hz, Ar); $^{13}$C-NMR (75.4 MHZ, CDCl$_3$): δ=16.47, 23.70, 25.94, 29.98, 67.47, 68.92, 70.66, 72.65, 76.38, 117.04, 120.3, 122.1, 134.73, 142.46, 149.90, 165.71, 176.46; FAB-MS: 341 (M—H)$^-$.

Preparation of Soluble Adhesion Molecules for Assaying Glycomimetics

Example 28

Preparation of L-selectin-IgG1

For preparing soluble L-selectin-IgG1 fusion protein, the genetic construct "ELAM-Rg" (Walz et al., *Science* 250:1132 (1990)) was used. The plasmid encoding the soluble fusion protein was transfected into COS-7 cells (ATCC) using DEAE-dextran. This method, and other molecular biology methods described herein, are further described in Ausubel et al. (*Current Protocols in Molecular Biology*, John Wiley, New York (1990)). Seven days after the transfection, the culture supernatant was recovered, freed from cells and cell fragments by centrifugation, transferred to 25 mM HEPES pH 7.0, 0.3 mM PMSF, 0.02% sodium azide and stored at +4° C.

Example 29

Preparation of P-selectin-IgG1

For the preparation of soluble P-selectin-IgG1 fusion protein, the genetic construct "CD62Rg" (Aruffo et al., *Cell* 67:35 (1991)), was used in a protocol analogous to that described above for soluble E-selectin.

Example 30

Preparation of CD4-IgG1

For the preparation of soluble CD4-IgG1 fusion protein, the genetic construct "CD4:IgG1 hinge" (Zettlemeissl et al., *DNA and Cell Biology* 9:347 (1990)) was used in a protocol analogous to that described above for soluble E-selectin.

Example 31

Cell Adhesion Assays on Recombinant, Soluble Adhesion Molecules Using HL 60 Cells 1. 96-well microtiter assay plates (Nunc Maxisorb) were incubated at room temperature for 2 hours with 100 μl of a goat antihuman IgG antibody (Sigma) diluted (1+100) in 50 mM Tris pH 9.5. After removing the antibody solution, washing was carried out once with PBS.
2. 150 μl of the blocking buffer were left in the wells at room temperature for 1 hour. The composition of the blocking buffer was as follows: 0.1% gelatin, 1% BSA, 5% calf serum, 0.2 mM PMSF, 0.02% sodium azide. After removing the blocking buffer, washing was carried out once with PBS.
3. 100 μl of cell culture supernatant of appropriately transfected and expressing COS cells was pipetted into each well. Incubation takes place at room temperature for 2 hours. After removing the cell culture supernatant, washing was carried out once with PBS.
4. 20 μl of binding buffer were added to the wells. The binding buffer has the following composition: 50 mM Hepes, pH 7.5; 100 mM NaCl; 1 mg/ml BSA; 2 mM MgCl$_2$; 1 mM CaCl$_2$; 3 mM MnCl$_2$; 0.02% sodium azide; 0.2 mM PMSF. 5 μl of the test substance were added by pipette, mixing was carried out by swirling the plate, and the plate was then incubated at room temperature for 10 minutes.
5. 50 ml of a HL60 cell culture containing 200,000 cells/ml were centrifuged at 350 g for 4 minutes. The pellet was resuspended in 10 ml of RPMI 1640 and the cells were centrifuged again. For labeling the cells, 50 μg of BCECF-AM (Molecular Probes) were dissolved in 5 μl of anhydrous DMSO; then 1.5 ml of RPMI 1640 were added to the BCECF-AM/DMSO solution. The cells were resuspended using this solution and incubated at 37° C. for 30 minutes. After centrifugation at 350 g for 2 minutes, the labeled cell pellet was resuspended in 11 ml of binding buffer and the resuspended cells were distributed in 100 μl aliquots into the microtiter plate wells. The plate was allowed to stand at room temperature for 10 minutes in order to allow the cells to sediment on the bottom of the assay plate. In the course of this, the cells have the opportunity to adhere to the coated plastic.

6. To stop the assay, the microtiter plate was immersed completely in the stop buffer (25 mM Tris, pH 7.5; 125 mM NaCl; 0.1% BSA; 2 mM $MgCl_2$; 1 mM $CaCl_2$; 3 mM $MnCl_2$; 0.02% sodium azide) at an angle of 450. The stop buffer was removed from the wells by inversion and the procedure was repeated twice more.

7. The BCECF-AM-labeled cells adhering in the wells were measured in a cytofluorimeter (Millipore), at a sensitivity setting of 4, an excitation wavelength of 485/22 nm and an emission wavelength of 530/25 nm.

Results $IC_{50}$ values for E-selectin and for P-selectin [mM]

| Compound | E-Selectin | P-Selectin |
|---|---|---|
| 20 | 2 | 2 |
| 23 | 2 | 2 |
| 24 | 5 | 5 |
| 25 | 5 | 5 |
| 26 | 5 | 5 |
| 28 | 5 | 5 |
| 28a | 5 | 5 |
| 29 | 5 | 5 |
| 36 | 5 | 3–5 |

Example 32

Assay of Adhesion Inhibition In Vivo

Induced adhesion of leukocytes is quantified in the mesenterium of the rat using an intravital microscopic investigation technique (Atherton et al. *J. Physiol.* 222;447 (1972); Sciffge in: Ersatz- und Ergänzungsmethoden zu Tierversuchen in der biomedizinischen Forschung, Schöffl, H. et al., (eds.) Springer, 1995 (in press). Long-term anesthesia is induced under inhalation ether anesthesia by intramuscular injection of urethane (1.25 mg/kg of body weight). After exposing the vessels (femoral vein for the injection of substances and carotid artery for blood pressure measurement), catheters are fastened into them. After this, the corresponding transparent tissue (mesenterium) is exposed according to the standard methods known in the literature and is arranged on the microscope stage and coated with warm liquid paraffin at 37° C. (Menger et al., *Immunology Today* 14:519 (1993)). The test substance is administered to the animal intravenously (10 mg/kg). The experimental increase in the blood cell adhesion is initiated by systemic administration of lipopolysaccharide (LPS, 15 mg/kg) 15 minutes after application of test substance, through cytokine activation (Foster et al., Agents and Actions 38:C77 (1993). The resulting increased adhesion of leukocytes on the endothelium is quantified directly by vital microscopy or with the aid of fluorescent dyes. All measurement operations are recorded on video camera and stored on a video recorder. Over a period of 60 minutes, the numbers of rolling leukocytes (i.e. all visibly rolling leukocytes, which are slower than the flowing erythrocytes) and the number of leukocytes adhering to the endothelium (residence period longer than 5 seconds) are determined every 10 minutes. Upon completion of the experiment, the anesthetized animals are painlessly euthanized by systemic injection of T61. For analysis, the results of in each case 8 treated animals are compared (in percentages) with 8 untreated animals (control group).

The invention has been disclosed broadly and illustrated in reference to representative embodiments described above. Those skilled in the art will recognize that various modifications can be made to the present invention without departing from the spirit and scope thereof.

The disclosure of all publications cited above are expressly incorporated herein by reference in their entireties to the same extent as if each were incorporated by reference individually. The disclosure of German Patent Application No. 19540388.6 (filed Oct. 30, 1995) for which benefit under 35 USC §119 is claimed, including the specification, claims and abstract, is expressly incorporated herein in its entirety.

What is claimed is:

1. A compound of the formula I

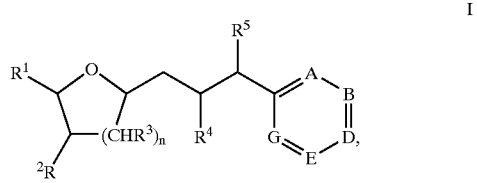

wherein:

n is 1 or 2;

$R^1$ is —H, —$CH_2OH$, or —$CH_3$;

$R^2$ and $R^3$ independently of one another are —H or —OH;

$R^4$ and $R^5$ independently of one another are —H, —OH—, -alkyl, —O-alkyl, —S-alkyl, —$NH_2$, —NH-alkyl, —N(alkyl)$_2$, —NH-aryl, —N(aryl)$_2$, —$OSO_3H$, —($CH_2$)$_r$-COOH, —($CH_2$)$_r$—COO-alkyl, —($CH_2$)$_r$CH(COO-alkyl)$_2$, —($CH_2$)$_r$CH(COOH)$_2$, or —($CH_2$)$_r$—$NH_2$, where r is an integer from zero to ten, or $R^4$ and $R^5$ together form an epoxide ring, or —$CHR_4$—$CHR_5$— is —CH=CH—;

A, B, D, E, and G independently are $CR^6$, $CR^7$, $CR^8$, $CR^9$, $CR^{10}$, or nitrogen, provided that only one of the variables A, B, D, E, and G may be nitrogen, and provided that when each of A, B, D, E, and G is —CH—, $R^5$ is not —H, —$NH_2$, or —OH, $R^6$, $R^7$, $R^8$, $R^9$, and $R^{10}$ independently of one another are:

(a) —H, -alkyl, —OH, —O-alkyl, —$NH_2$, —NH-alkyl, —N(alkyl)$_2$, —NH-aryl, —N(aryl)$_2$, —F, —Cl, —Br, —I, —COO-alkyl, —CO—$NH_2$, —COOH, —$OSO_3H$, 4-hydroxypiperidin-4-yl, —($CH_2$)$_m$—COOH, —($CH_2$)$_m$COO-alkyl, or —($CH_2$)$_m$—CH(COO-alkyl)$_2$, (b) —($CH_2$)$_m$—CH(COOH)$_2$, where m is an integer from zero to ten, (c) —($CH_2$)$_p$—$NH_2$, where p is an integer from one to ten, or (d) a group of the formula II, III, IV, V, VI, or VII,

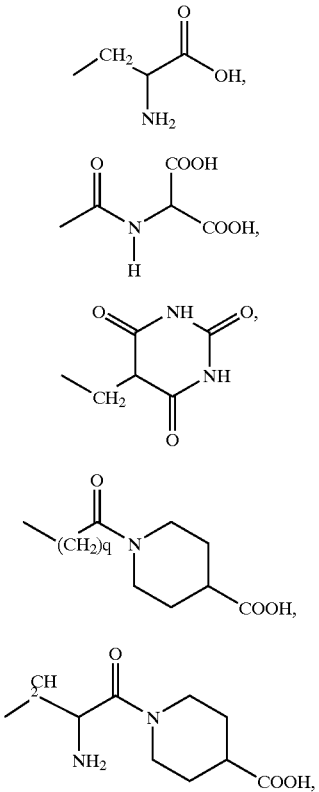

X1 and X2 independently of one another are H or an oligopeptide;

or two of the variables $R^6$, $R^7$, $R^8$, $R^9$, or $R^{10}$, provided they are adjacent, together form a carboxymethyl-substituted imidazole ring or a crown ether ring.

2. A compound according to claim 1, wherein $R^4$ and $R^5$ are both H, or —CH $R^4$—CH $R^5$— is —CH═CH—.

3. A compound according to claim 2, wherein A, B, G and E are C—H and D is $CR^8$.

4. A compound according to claim 3, wherein $R^8$ is selected from the group consisting of II, III, IV, V, VI, and VII.

5. A compound according to claim 4, wherein $R^8$ is II.

6. A pharmaceutical composition comprising a compound according to claim 1, together with a pharmaceutically acceptable excipient.

7. A compound according to claim 1, wherein $R^1$, $R^2$, and $R^3$ have the same absolute configuration as in L-fucose, D-mannose, or D-ribose.

* * * * *